United States Patent [19]

Strickland

[11] Patent Number: 5,135,490
[45] Date of Patent: Aug. 4, 1992

[54] METHOD AND SYSTEM FOR EFFECTING WEDGING OF A BRONCHOALVEOLAR LAVAGE CATHETER

[76] Inventor: Richard D. Strickland, 8890 S. Sheffield Way, Sandy, Utah 84093

[21] Appl. No.: 633,266

[22] Filed: Dec. 21, 1990

[51] Int. Cl.$^5$ ............................................. A61M 31/00
[52] U.S. Cl. ...................................... 604/50; 604/48; 604/280; 128/898
[58] Field of Search ........................ 604/27, 28, 35, 48, 604/49, 50, 54, 264, 270, 280; 128/897-898

[56] References Cited

U.S. PATENT DOCUMENTS

| | | | |
|---|---|---|---|
| 4,344,436 | 8/1982 | Kubota | 604/264 |
| 4,351,328 | 9/1982 | Bodai | 128/202.16 |
| 4,846,191 | 7/1989 | Brockway et al. | 128/748 |
| 4,886,496 | 12/1989 | Conoscenti et al. | 604/96 |
| 4,981,470 | 1/1991 | Bombeck, IV | 128/635 |
| 4,981,477 | 1/1991 | Schon et al. | 604/264 |

OTHER PUBLICATIONS

Caughley et al., "Non-Bronchoscopic Bronchio Alveoli Lavage for the Diagnosis of Pneumocystitis Carinii Pneumonia in the Acquired Immune Deficiency Syndrome", 88 Chest 659-62 (Nov. 1985).
Sobonya et al., "Detection of Fungi and other Pathogens in Immunocompromised Patients by Bronchio Alveoli Lavage in an Area Endemic for Coccidioidomycosis", 97 Chest 1349-55 (Jun. 1990).
Guerra et al., "Use of Bronchio Alveoli Lavage to Diagnosis Bacterial Pneumonia in Mechanically Ventilated Patients", 18 Critical Care Medicine, 169-73 (1990).
Mehta et al., "The High Price of Bronchoscopy: Maintenance and Repair of the Flexible Fiber Optic Bronchoscope", 98 Chest 448-54 (Aug. 1984).
American Thoracic Society, "Clinical Role of Bronchoalveolar Lavage in Adults with Pulmonary Disease", 142 American Review of Respiratory Disease, 481-486 (1990).
Martin, Walter R. et al., "Tracheal Catheters in Patients with Acquired Immunodeficiency Syndrome for the Diagnosis of Pneumocystis Carinii Pneumonia", 96 Chest 29-32 (Jul. 1990).

*Primary Examiner*—C. Fred Rosenbaum
*Assistant Examiner*—C. Maglione
*Attorney, Agent, or Firm*—Workman Nydegger Jensen

[57] ABSTRACT

The end of a bronchoalveolar lavage catheter is coupled to an adaptor manifold which has a pressure port that allows communication to occur between the lumen at the center of the bronchoalveolar lavage catheter and an air pressure tube leading to a pressure transducer. Air pressure impulses from the air passageways of a patient are then communicated to the pressure transducer and converted into electronic signals capable of providing useful feedback to medical personnel. One form of feedback constitutes real-time pressure waveforms which are monitored to detect the existence at the tip of the bronchoalveolar lavage catheter of significant wedging-related conditions of interest to medical personnel attempting to effect wedging of the distal tip of the bronchoalveolar lavage catheter. The significant wedging-related conditions comprise conditions of correct wedging, ineffectual wedging, precluded wedging and overwedging. The proximal end of the bronchoalveolar lavage catheter is manipulated on the basis of the predetermined wedging related conditions detected in order thereby to verify correct wedging prior to the infusion of sampling fluid.

52 Claims, 11 Drawing Sheets

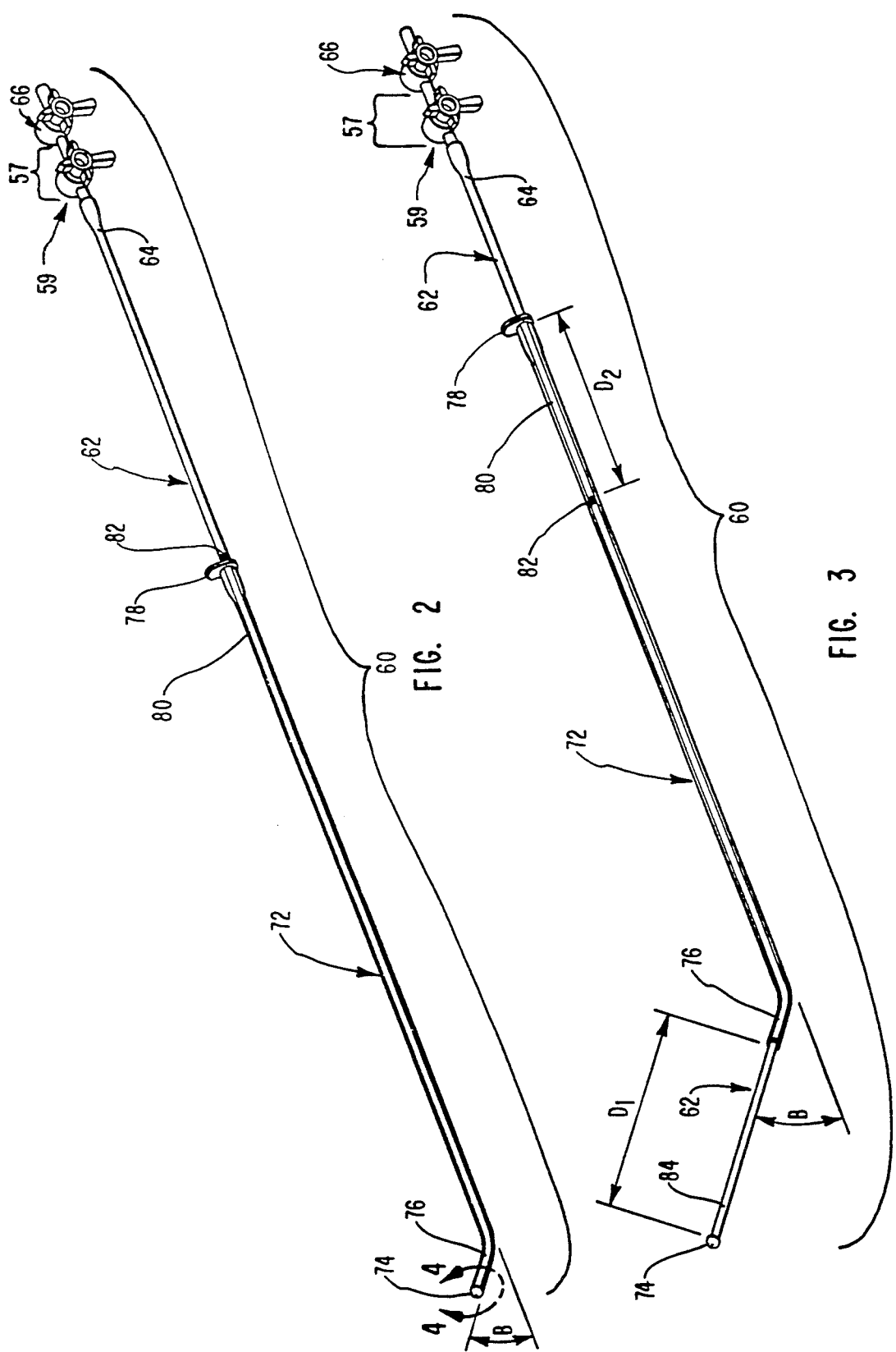

METHOD AND SYSTEM FOR EFFECTING WEDGING OF A BRONCHOALVEOLAR LAVAGE CATHETER

RELATED APPLICATIONS

The subject matter of this application relates to the subject matter of copending U.S. patent application No. 631638 for BRONCHOALVEOLAR LAVAGE CATHETER and U.S. patent application No. 633267 for CATHETER PLACEMENT LOCKING AND SEALING DEVICE, both filed contemporaneously herewith on Dec. 21, 1990, the latter of which is incorporated herein by reference.

BACKGROUND

1. Field of the Invention

This invention relates to the diagnosis of abnormal & conditions in the lungs by conducting bronchoalveolar lavage. More particularly the present invention relates to a method and system for effecting and confirming proper wedging of the distal tip of a bronchoalveolar lavage catheter in a bronchiole of a lung of a patient.

2. Background Art

The technique of bronchoalveolar lavage has become common in the diagnosis of infections and other abnormalities in the alveoli at the terminus of the bronchioles in the lungs of a patient. In bronchoalveolar lavage (BAL), a sterile fluid is infused in aliquots of about 30 ml. each through the upper respiratory system of a patient into the portion of the lungs thereof designated for study. The fluid infused is then aspirated, cultured, and examined in order to isolate and identify infections, fungi, cells, and other signs of inflammation thusly flushed from the walls of the alveoli. Only about 40 to 60% of each infused aliquot can be aspirated. Thus in studies which require large volumes of aspirated fluid, a total infusion of from 30 to about 500 ml. may be required. A helpful background statement on the nature and useful findings related to the use of bronchoalveolar lavage is the American Thoracic Society, "Clinical Role of Bronchoalveolar Lavage in Adults with Pulmonary Disease", 142 AMERICAN REVIEW OF RESPIRATORY DISEASE, 481-486 (1990).

In order to effect the infusion of solution, it has in the past been the practice to utilize a bronchoscope to visually observe the advancement of a catheter through the upper respiratory system of a patient and the branching of the bronchi into a selected bronchiole. During this advancement process, the size of the air passage through which the distal tip of the bronchoscope is advanced gradually decreases until the distal tip of the bronchoscope wedges within the walls of a single bronchiole. This wedge is visually inspected using the bronchoscope, and thereafter the infusion and aspiration of solution is effected through a working lumen in the bronchoscope.

Drawbacks arise, however, in relation to the use of a bronchoscope in this procedure. First, the bronchoscope itself is a very expensive piece of equipment. As a result, it is not practical to dispose of the device following a single use. Instead, the bronchoscope must be reused in order to distribute its expense over a number of procedures. Routine heat-based sterilization, however, cannot be used. Instead, procedures must be employed which are particularly adapted to the delicate nature of the materials comprising the bronchoscope. These sterilization procedures require approximately twenty-four hours to complete, so that a single costly bronchoscope can be utilized at a given medical establishment only once a day. Thus, a plurality of bronchoscopes must be maintained by a medical establishment, if bronchoalveolar lavage is to be performed more than once a day.

In addition to being extremely delicate in the face of normal sterilization conditions, bronchoscopes are very susceptible to breakage through incorrect use. Like the device itself, repairs on the bronchoscope are extremely expensive. A reference discussing the sources of damage to flexible fiber optic bronchoscopes is Mehta, et al., "The High Price of Bronchoscopy: Maintenance and Repair of the Flexible Fiber Optic Bronchoscope," 98 CHEST 448-54 (August 1984).

Recent literature has forecast a rise in the frequency with which medical practitioners can be expected to resort to the use of bronchoalveolar lavage. The increased incidence of acquired immune deficiency syndrome (AIDS) and other therapeutic-related immunocompromising treatments, such as chemotherapy, gives rise to a large number of patients $ susceptible to multiple and exotic lung infections. An accurate diagnosis of the identity of these infections is essential, if the patient is to be effectively medicated. Typical of the literature discussing efforts at isolating lung infections in AIDS and other immunocompromised patients are the following:

Caughley, et al., "Non-Bronchoscopic Bronchio Alveoli Lavage for the Diagnosis of Pneumocystitis Carinii Pneumonia in the Acquired Immune Deficiency Syndrome", 88 CHEST 659-62 (November 1985).

Sobonya, et al., "Detection of Fungi and other Pathogens in Immunocompromised Patients by Bronchio Alveoli Lavage in an Area Endemic for Coccidioidomycosis", 97 CHEST 1349-55 (June 1990).

Guerra, et al., "Use of Bronchio Alveoli Lavage to Diagnose Bacterial Pneumonia in Mechanically Ventilated Patients", 18 CRITICAL CARE MEDICINE, 169-73 (1990).

Some difficulties have also been experienced in effecting a clear diagnosis of conditions in the lung due to contamination of the equipment for conducting the bronchoalveolar lavage as the distal end of that equipment is passed through the upper respiratory system of a patient to the lung segment selected for study. In the process of that passage, the exterior of the distal end of the catheter by which infusion and aspiration is actually effected becomes contaminated with micro-organisms from the upper respiratory system of the patient. As a result, the fluid samples aspirated from the lungs thereafter are frequently compromised by cultures of organisms not actually located in the alveoli.

When a bronchoscope is not utilized, problems have been experienced in locating the distal tip of the sampling catheter in a specific preselected lung to be studied, placement in the left lung being particularly difficult due to inherent anatomical structure of the bronchi. Fluoroscopic and X-ray methods for verifying the location of a distal tip can to an extent be useful in assisting in directing the distal tip into a specific preselected lung. Nevertheless, these methods are totally incapable of replacing the primary value of bronchoscope use, namely the verification of distal tip wedging in a bronchiole of the patient to the extent required for successful infusion and aspiration of fluid. Fluoroscopic and X-ray methods for effecting placement are also complicated to utilize, and may be limited by availability to large medical institutions.

In conducting bronchoalveolar lavage several difficulties arise in effecting and verifying correct wedging of the distal tip of the catheter employed. In correct wedging, the walls of the bronchiole engage the full circumference of the resultant seal produces of the air passageways distal of the tip a closed space that permits optimal recovery of sampling fluid infused into those passageways. If the wedging of the distal tip of the bronchoalveolar lavage catheter has been correctly effected, these air passageways should be isolated from all others in the lung of the patient.

Correct wedging does not, however, result merely due to the advancement of a bronchoalveolar lavage catheter into the lung of a patient. In the absence of correct wedging, it is impossible to recover much or even any of the sampling fluid infused. Significant quantities of such fluid must be left in the lung of the patient after the procedure. Such non-aspirated sampling fluid can itself pose health hazards by stimulating pneumonia or other lung infections.

Ineffective wedging takes several forms. First, the shape or the orientation of the distal tip of the bronchoalveolar lavage catheter relative to the walls of the bronchiole in which it is lodged may be such that those walls do not engage the full circumference of the catheter tip. Under such circumstances, the air passageways distal of the wedging site are not isolated from the rest of the lungs, and the suction required for withdrawing the sampling solution cannot be effected. In addition, excess sampling solution injected into those air passageways can escape therefrom between the catheter tip and the bronchiole walls, thereby to settle in other portions of the lung than the portion upon which testing is being conducted. This escaped fluid, as well as sampling fluid not recovered from the targeted portion of the lung, presents the health hazards described already.

Where bronchoalveolar lavage is conducted without using a bronchoscope, it is common to attempt to confirm wedging merely from physical resistance to the advancement of the bronchoalveolar lavage catheter. Nevertheless, as appreciated from the discussion of ineffective wedging, it is possible for advancement of a bronchoalveolar lavage catheter to be precluded, but without securing a full circumferential seal on the distal tip of the catheter.

There are other circumstances in which one may be unable to recover the infused sampling fluid. For example, a full circumferential seal about the catheter tip may be effected by the walls of a bronchiole, but the action of respiration may cause one wall of the bronchiole, or even some other structure, to be drawn against the aperture opening into the lumen of the catheter through the distal tip thereof. Typically, this is most likely to occur when the aperture in the tip is disposed close to a wall of the bronchiole. Whenever this occurs, it is predictable that sampling fluid, if infused, could not then be aspirated. The sampling fluid would thus remain in the lungs. As used herein and in the appendant claims, the blocking of the opening into the distal tip of a bronchoalveolar lavage catheter in the manner described will be referred to as an "overwedged" condition.

Overwedging also occurs with regularity where the distal tip of the bronchoalveolar lavage catheter fails to negotiate a branching in the air passageway in which it is being advanced. This can result in precluded wedging, but in many instances the tissue in the space between the two branches of the air passageway directly enters the aperture through the tip of the catheter and then blocks the withdrawal of infused sampling fluid. The positive pressure of the infused sampling fluid nevertheless pushes aside the soft tissue of the bronchiole wall, so that fluid is admitted into the contiguous air passageways. In this respect, overwedging creates the functional equivalent of a one-way valve, which unfortunately enables a medical practitioner to fill a portion of the lung with fluid which cannot be removed.

It is possible using bronchoscopy to detect these types of overwedging, but bronchoscopy adds substantially to the cost of conducting bronchoalveolar lavage. Thus, while the creation of an overwedged condition can be expected with some degree of regularity, only through the use of expensive bronchoscopy will some of such conditions be detected before a full aliquot of ultimately unrecoverable sampling fluid is infused into the lungs.

OBJECTS AND BRIEF SUMMARY OF THE INVENTION

One object of the present invention is to improve the accuracy of diagnostic efforts directed to inflammations and other abnormalities in the lungs.

It is a related object of the present invention to increase the ease of conducting bronchoalveolar lavage.

Another object of the present invention is to facilitate the use of bronchoalveolar lavage without resort to costly bronchoscopic techniques.

Yet another object of the present invention is to reduce the health risks to a patient undergoing bronchoalveolar lavage from those associated with sampling fluid which cannot be withdrawn from the lungs.

A further object of the present invention is to permit an evaluation of the quality of wedging effected during bronchoalveolar lavage, prior to the infusion of any sampling fluid.

An additional object of the present invention is to confirm the existence of proper wedging conditions at the tip of a bronchoalveolar lavage catheter, and to detect the existence of overwedging, ineffective wedging, or precluded wedging before sampling fluid is infused.

It is yet another object of the present invention to permit medical personnel conducting bronchoalveolar lavage to evaluate wedging conditions at the distal tip of the bronchoalveolar lavage catheter without resorting to expensive bronchoscopy.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

The present invention is directed to a system and method for performing bronchoalveolar lavage with a variety of bronchoalveolar lavage catheters. In each instance, however, the proximal end of the bronchoalveolar lavage catheter is coupled to an adapter manifold which has a pressure port that allows communication to occur between the lumen at the center of the bronchoalveolar lavage catheter and an air pressure tube leading to a pressure transducer. In this way, the pressure distal of the tip of the bronchoalveolar lavage catheter is communicated from the aperture in the tip, through the lumen of the catheter, the pressure port, and the air pressure line, to the pressure transducer. Air pressure impulses from the lungs of the patient are then converted by the pressure transducer into electronic signals capable of being processed into any form of output useful to medical personnel. Such forms of output can include real time pressure waveforms presented on a monitor or in a printout. Other forms of indicators, such as auditory signals and lights are also appropriate.

One embodiment of a bronchoalveolar lavage catheter useable with the inventive method involves a sampling catheter disposed inside an insertion sheath. These are together advanced through the upper respiratory system of the patient after which the sampling catheter is advanced distally, out of the insertion sheath and into a preselected lung of the patient. In passing through the upper respiratory system, the aperture at the tip of the sampling catheter can become blocked with a plug of contaminated mucus. Accordingly, in order to reduce contaminated and to clear the aperture for effective airway pressure monitoring, a small amount of sampling fluid is used to flush the aperture at the tip of the sampling catheter before the tip is advanced and wedged in a bronchiole. Thereafter, pressure monitoring is undertaken on a continuous basis until satisfactory wedging of the tip of the catheter is achieved.

A baseline pressure waveform is first derived which can thereafter be compared with pressure waveforms obtained subsequently, during the effort to effect correct wedging. Generally, the baseline pressure waveform comprises a recurring series of alternate high pressure peaks and low, but positive, pressure troughs reflecting air passageway pressure variations caused by natural breathing efforts or by mechanical ventilation.

The bronchoalveolar lavage catheter is advanced into the air passageway of the patient seeking to wedge the distal tip of the catheter into an appropriately sized bronchiole. The pressure waveforms detected through the bronchoalveolar lavage catheter change from those in the baseline pressure waveform as the tip of the catheter interacts with the walls of the bronchiole. The operator advancing the sampling catheter monitors these changes to detect those that are characteristic of distinct wedging-related conditions of interest.

The wedging-related conditions of interest naturally include correct wedging in which the full circumference of the tip of the bronchoalveolar lavage catheter makes sealing contact with the walls of a bronchiole. Also of interest are ineffective wedging, in which suction effective to aspirate sampling fluid cannot be applied to the air passageways distal of the catheter tip, and precluded wedging, in which the bronchoalveolar lavage catheter encounters physical resistance to advancement without actually achieving correct wedging. A final wedging-related condition of interest is the overwedged condition in which tissue from the walls of the bronchiole adjacent the catheter tip is able to block the aperture at the tip of the bronchoalveolar lavage catheter during part or all of the respiratory cycle of the patient.

The waveforms observed during ineffective or precluded wedge are substantially similar to the baseline waveform. The waveforms observed during precluded wedging, however, take on the appearance of dampened versions of the baseline waveform, sharing the general shape and periodicity thereof, but exhibiting generally lower peaks and higher troughs than the baseline pressure waveform. Overwedging results in a pressure waveform that takes the form of overly-damped baseline pressure waveform having, in particular, lengthy, flat-bottomed troughs, and in some instances no periodicity or resemblance to the base line pressure waveform whatsoever.

Based on the resistance encountered in advancing the bronchoalveolar lavage catheter, and on the pressure waveforms observed, bronchoalveolar lavage is undertaken, or the catheter is withdrawn a distance, rotated, and a new wedge is attempted. In every case, prior to infusing sampling fluid, correct wedging is verified using the described pressure monitoring techniques.

The present invention may be employed effectively with an alternative form of a bronchoalveolar lavage catheter in which an inflatable, flexible cuff is attached to and encircles the sides of the sampling catheter proximal of the distal end. The cuff is selectively inflatable through a second lumen within the sampling catheter. Use of the inflatable cuff allows wedging to occur in a larger bronchiole than would be possible when wedging with the catheter tip directly. The wedging in a larger bronchiole permits sampling from a larger fraction of the lung of the patient.

The same pressure waveform considerations described above are applicable in order to verify that correct wedging has occurred with the cuff embodiment of a bronchoalveolar lavage catheter. Underinflation of the flexible cuff may result in ineffective wedging which it is desirable to detect prior to infusing fluid. Over inflation of the cuff may cause the cuff to balloon forward of the distal tip, and thereby be drawn into the aperture therethrough when the aspiration is attempted. The latter circumstance would be reflected in a pressure waveform indicative of overwedging.

The present invention is useable with bronchoalveolar lavage conducted on patients with or without an intubated endotracheal tube. Where intubation is involved, the proximal end of the endotracheal tube can be provided with a locking mechanism for precluding longitudinal displacement of the catheter once it is correctly wedged.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 2 is a perspective view of one embodiment of a composite bronchoalveolar lavage catheter for use in the system of FIG. 1 with the distal ends of the insertion sheath and of the sampling catheter in sealing engagement;

FIG. 3 is a perspective view of the bronchoalveolar lavage catheter shown in FIG. 2 with the distal end of the sampling catheter extended out of the distal end of the insertion sheath;

FIG. 7b is an enlarged detailed view of the distal tip of the bronchoalveolar lavage catheter shown in FIG. 7a;

DETAILED DESCRIPTION OF THE PREFERRED EMBODIMENTS

Figure 1:
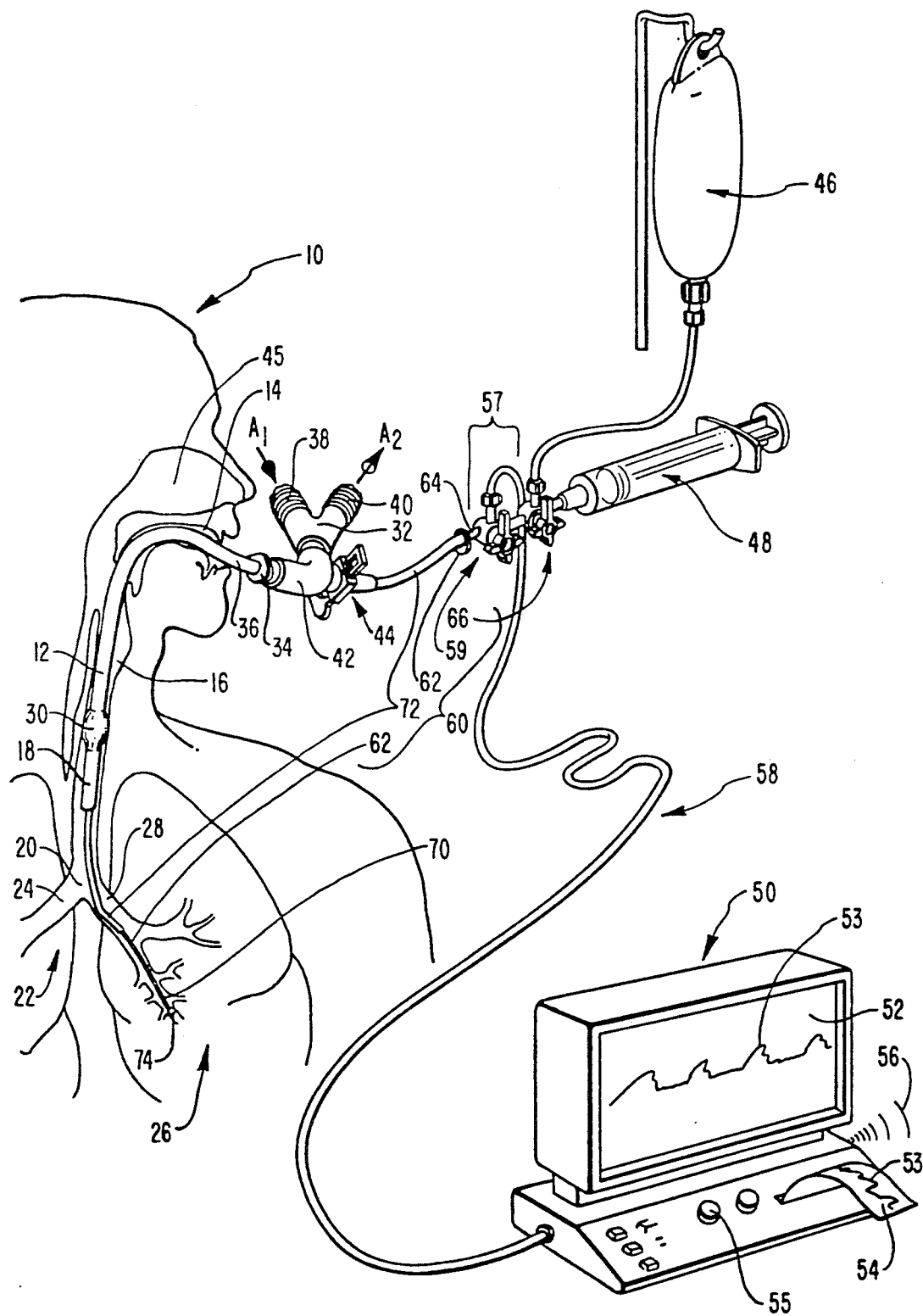
FIG. 1 is a schematic drawing of a system for conducting bronchoalveolar lavage utilizing the inventive method and system.

FIG. 1 illustrates the environment in which the inventive system and method are employed in relation patient 10 intubated with an endotracheal tube 12. Although intubation is not required in order to perform bronchoalveolar lavage with the inventive method and system disclosed herein, intubation may be employed expressly for the purpose of facilitating the procedure of bronchoalveolar lavage. Generally, however, intubation is undertaken in order to provide ongoing mechanical ventilation of a patient.

As seen in FIG. 1, endotracheal tube 12 extends through mouth 14 and trachea 16 of the upper respiratory system of patient 10, terminating at a distal end 18 above the point 20 at the first bifurcation of trachea 16 into the right lung 22 through right mainstem bronchus 24 and into left lung 26 through left mainstem bronchus 28. Typical sub-branchings of the bronchia are shown in FIG. 1 for illustrative purposes in relation to the sub-branching of left mainstem bronchus 24 into left lung 26.

Distal end 18 of endotracheal tube 12 is provided with a balloon 30 which, when inflated, engages the walls of trachea 16 to facilitate mechanical ventilation of patient 10 through a Y-connector 32 coupled to a standard endotracheal tube adapter 34 at proximal end 36 of endotracheal tube 12. Air from the ventilating apparatus for patient 10 enters endotracheal tube 12 through a first leg 38 of Y-connector 32 as indicated in FIG. 1 by arrow $A_1$. Correspondingly, air is returned to the ventilating apparatus from patient 10 through a second leg 40 of Y-connector 32 as shown in FIG. 1 by arrow $A_2$.

An elbow coupling 42 connects endotracheal tube adapter 34 with Y-connector 32 and is provided at a point on the outer radius thereof with a bronchoalveolar lavage catheter access port 44 through which a bronchoalveolar lavage catheter can be entered into endotracheal tube 12 and advanced therethrough into a preselected lung of patient 10 without losing the positive end expiratory pressure (PEEP) often required during mechanical ventilation. According to one aspect of the inventive system, bronchoalveolar lavage catheter access port 44 is provided with a locking means for fixing the longitudinal position of a bronchoalveolar lavage catheter entered through bronchoalveolar lavage catheter access port 44 into a lung of patient 10. The locking means is manually actuatable to prevent movement of the bronchoalveolar lavage catheter relative to endotracheal tube 12, thereby maintaining correct wedging if such has been effected.

It must be emphasized that use of the inventive system and methods disclose herein is not limited to use with patients undergoing mechanical ventilation, or even patients in whom intubation with an endotracheal tube has occurred. Indeed, bronchoalveolar lavage can be conducted with the inventive system and method through the nasal passages 45 of a patient, such as patient 10, rather than through the mouth 14 thereof.

Typically, as illustrated in FIG. 1, bronchoalveolar lavage is to be performed on a portion of left lung 26 of patient 10. In the process, a sterile fluid from a reservoir 46 thereof is infused in individual aliquots using a syringe 48. The fluid of each infusion is then aspirated using either syringe 48 or the wall vacuum in the medical institution in which the bronchoalveolar lavage is conducted.

According to another aspect of the present invention, means are provided for monitoring air passageway pressure distal of the tip of a bronchoalveolar lavage catheter. As shown in FIG. 1 by way of example and not limitation, a gas pressure monitor 50 containing a pressure transducer (not shown) is so coupled to bronchoalveolar lavage catheter 60 as inform medical personnel of the air pressure patterns arising in the air passageways of patient 10 distal of the distal tip of a bronchoalveolar lavage catheter. Accordingly, gas pressure monitor 50 could include a cathode ray tube screen 52 for exhibiting real time pressure waveforms 53 or a printout 54 of continuous paper, if a permanent record of waveforms 53 is desirable. Alternatively, or in addition thereto, gas pressure monitor 50 may be provided with indicator lights 55 and mechanisms for creating audible tones 56 as where the evaluation of waveforms 53 is undertaken without substantial operator intervention utilizing microprocessor-based artificial intelligence software.

In one aspect of the means for monitoring, means are provided for coupling gas pressure monitor 50 to the lumen inside a bronchoalveolar lavage catheter. As shown in FIG. 1 by way of illustration and not limitation, the means for coupling comprises an adaptor manifold 57 to be coupled at the proximal end of a bronchoalveolar lavage catheter and gas pressure tubing 58 communicating with the pressure transducer in gas pressure monitor 50. As shown in FIG. 1, adaptor manifold 57 includes a selectively operable pressure stopcock 59 to be described in more detail subsequently.

With gas pressure tubing 58 attached to one output of pressure stopcock 59, the pressure transducer of gas pressure monitor 50 can be selectively coupled to the lumen in the bronchoalveolar lavage catheter with which the means for monitoring is employed. Under such conditions, the pressure transducer of gas pressure monitor 50 converts pressure impulses from the tip of a bronchoalveolar lavage catheter into pressure waveforms 53 by which the correct wedging or other disposition of that bronchoalveolar lavage catheter can be effected and verified. The manner in which pressure waveforms 53 contribute to this objective will also be discussed subsequently.

Illustrated in FIG. 1 is one embodiment of a bronchoalveolar lavage catheter 60 useable in the system and the method of the present invention. Basically, bronchoalveolar lavage catheter 60 is an assembly of subcomponents functioning together for the purpose stated. Nevertheless, it will be understood from the disclosure which follows that some or all of the components thereof may be eliminated from bronchoalveolar lavage catheter 60 while yet incorporating teachings of the present invention. Accordingly, as shown in FIG. 1, bronchoalveolar lavage catheter 60 includes an inner sampling catheter 62 so sized and configured as to extend from a bronchiole in left lung 26 of patient 10 through the upper respiratory system.

According to one aspect of the present invention, at proximal end 64 of sampling catheter 62, means are provided for infusing and aspirating fluid through sampling catheter 62 into the lung of a patient. As shown by way of example and not limitation, a sampling stopcock 66 is coupled to proximal end 64 of sampling catheter 62. Sampling stopcock 62 is capable of connection to reservoir 46 and to syringe 48 in such a manner as to selectively place syringe 48 alternately in communication with reservoir 46 or with proximal end 64 of sampling catheter 62.

In another aspect of the present invention, a pressure stopcock 59 comprising a portion of the inventive means for monitoring airway pressure distal of the tip of a bronchoalveolar lavage catheter is located between proximal end 64 of sampling catheter 62 and sampling stopcock 66. Pressure stopcock 59 is capable of selectively placing proximal end 64 of sampling catheter 62 in communication alternately with air passageway pressure monitor 50 or with sampling stopcock 66. In the latter condition, it is impossible to infuse and aspirate fluid from reservoir 46 through sampling catheter 62. When the process of infusion and aspiration is not ongoing, the placement of air passageway pressure monitor 50 in communication with the lumen of sampling catheter 62 by the appropriate manipulation of pressure stopcock 59 enables a medical practitioner to evaluate the air pressure patterns in air passageways of patient 10 distal of the tip of distal end 70 of sampling catheter 62. The structures are used to effect and verify correct wedging of the tip of distal end 70 of sampling catheter 62 in a bronchiole of patient 10.

Bronchoalveolar lavaqe catheter 60 is provided with means for directing distal end 70 of sampling catheter 62 into a preselected lung of patient 10, while also protecting the outside of sampling catheter 62 from contamination during the advancement of distal end 70 of sampling catheter 62 through the upper respiratory system of patient 10. As shown by way of example, and not limitation, bronchoalveolar lavage catheter 60 comprises an elongated outer catheter or insertion sheath 72 so sized and configured as to encircle sampling catheter 62 and to be capable of extending from a location below the point 20 at the first bifurcation of trachea 16 through the upper respiratory system of patient 10.

The structure of insertion sheath 72 and interaction thereof with sampling catheter 62 during the process of conducting bronchoalveolar lavage with bronchoalveolar lavage catheter 60 will be more clearly appreciated by reference first to FIG. 2. There sampling catheter 62 is disposed within insertion sheath 72 with the tip 74 at distal end 70 of sampling catheter 62 at distal end 76 of insertion sheath 72. The ability of bronchoalveolar lavage catheter 60 to effect bronchoalveolar lavage in a preselected lung of patient 10 is dependent both upon the structure of distal end 76 of insertion sheath 72 and upon the composition of which insertion sheath 72 is formed.

As seen in FIG. 2, distal end 76 of insertion sheath 72 is displaced at a predetermined bend angle B to the longitudinal axis of insertion sheath 72. A direction indicator 78 at proximal end 80 of insertion sheath 72 projects from insertion sheath 72 in the same radial direction as the radial direction at which distal end 76 of insertion sheath 72 departs from the longitudinal axis thereof.

Insertion sheath 72 is comprised of a relatively rigid material, such as ethyl vinyl acetate. In this manner, insertion sheath 72 will be design possess sufficient structural rigidity as to be capable, when disposed in the warm, upper respiratory system of patient 10, of exhibiting at distal end 76 one-to-one rotation about the longitudinal axis of insertion sheath 72 relative to proximal end 80 thereof. When insertion sheath 72 is disposed in the upper respiratory system of patient 10 as shown in FIG. 1, the rotation of proximal end 80 of insertion sheath 72 about the longitudinal axis thereof will result in a corresponding identical rotation of distal end 76 of insertion sheath 72 about the longitudinal axis thereof. Direction indicator 78 will at all times be oriented in the radial direction at which distal end 76 departs from the longitudinal axis of insertion sheath 72. By utilizing this feature of bronchoalveolar lavage catheter 60, sampling catheter 62 can be advanced for the purpose of conducting bronchoalveolar lavage into a preselected one of the lungs 22, 26 of patient 10.

A position indicator mark 82 is provided on sampling catheter 62 at the location thereupon which is disposed at proximal end 80 of insertion sheath 72 when tip 74 of sampling catheter 62 is located at distal end 76 of insertion sheath 72. As will be discussed in further detail, in this relative position of sampling catheter 62 and insertion sheath 72, tip 74 sealingly engages distal end 76 of insertion sheath 72.

As becomes clear by reference to FIG. 3, however, insertion sheath 72 and sampling catheter 62 are relatively sized so that sampling catheter 62 can slide freely within insertion sheath 72. Thus, sampling catheter 62 can be advanced within insertion sheath 72, so that tip 74 moves a distance $D_1$ away from distal end 76 of insertion sheath 72 revealing distal end 84 of sampling catheter 62. Correspondingly, position indicator mark 82 is advanced into proximal end 80 of insertion sheath 72 by distance $D_2$ equal to the distance $D_1$.

In use, once insertion sheath 72 is disposed in the upper respiratory tract of patient 10, and insertion sheath 72 is rotated about the axis thereof to orient direction indicator 78 toward a preselected one of lungs 22, 26, sampling catheter 62 is advanced within insertion sheath 72 in the manner illustrated in FIG. 3. Doing so necessarily results in distal end 84 of sampling catheter 62 advancing into the preselected one of lungs 22, 26. Thus, the initial direction in which distal end 84 of sampling catheter 62 advances from insertion sheath 72 is determined by the orientation of the bend at distal end 76 of insertion sheath 72. Thereafter, distal end 84 of sampling catheter 62 advances into the preselected one of lungs 22, 24 on the basis of its own structure, which desirably is more pliable than that of insertion sheath 72.

According to another aspect of the present system, sampling catheter 62 comprises a first closure means located at distal end 70 thereof for sealing distal end 76 of insertion sheath 72 when insertion sheath 72 is disposed encircling sampling catheter 62 with distal end 70 of sampling catheter 62 at distal end 76 of insertion sheath 72. This is the relative positioning of sampling catheter 62 and insertion sheath 72 shown in FIG. 2 with position indicator mark 82 being located just at the terminus of proximal end 80 of insertion sheath 72. Tip 74 comprises a radially symmetrical insert secured in distal end 70 of sampling catheter 62.

When insertion sheath 72 and sampling catheter 62 are in the relative positions illustrated in FIG. 2, insertion sheath 72 with sampling catheter 62 disposed therein can be advanced through the upper respiratory system of patient 10 while protecting the outer surface of sampling catheter 62 from contamination by microorganisms residing within the upper respiratory system. Only after distal end 76 of insertion sheath 72 has been rotated so as to be directed into the preselected one of lungs 22, 24 and has then thereafter been advanced beyond the point 20 at which trachea 16 initially branches, is sampling catheter 62 advanced out of insertion sheath 72, exposing the outer surface of sampling catheter 62 to ambient contaminations. Nevertheless, at this point in the respiratory system of patient 10 the chances that micro-organisms inhabiting the upper respiratory system will attach to the outer surface of sampling catheter 62 are substantially reduced, contributing to more accuracy in the samples recovered through sampling catheter 62.

During the advancement of sampling catheter 62 out of insertion sheath 72 and into the preselected one of lungs 22, 24, the size of the air passage through which tip 74 is advanced gradually decreases until the lead surface of tip 74 wedges within the walls of a single bronchiole. The shape of tip 74 assists in the process of initial wedging by continuing to deflect tip 74 away from the walls of the air passageway into which sampling catheter 62 is being advanced, until such time as the walls of that air passageway uniformly surround and close upon the outer circumference of tip 74. Thereafter, the mushroom-shaped cross-section of tip 74 prevents the inadvertent withdrawal of tip 74 from its wedged position. Tissue from the wall of the air passageway in which tip 74 is wedged presses against the full outer circumference of tip 74. This tissue tends to hold tip 74 in a wedging position in a desirable manner. Nevertheless, the smooth shape of tip 74 has the effect of minimizing trauma as wedging is actually effected. Thereafter, the infusion and aspiration be safely and reliably undertaken.

The steps for utilizing bronchoalveolar lavage catheter 60 will be discussed first with reference to FIG. 4. Insertion sheath 72 with sampling catheter 62 disposed therein in the manner shown in FIG. 2 is introduced into endotracheal tube 12 through an appropriate coupling, such as elbow coupling 42 and bronchoalveolar lavage catheter access port 44. The assembly of insertion sheath 74 with sampling catheter 62 therein is then advanced through the upper respiratory system of patient 10 to distal end 18 of endotracheal tube 12. Thereafter, the assembly of insertion sheath 72 and sampling catheter 62 therewithin is advanced out of distal end 18 of endotracheal tube 12 into trachea 16 of the upper respiratory system of patient 10. The advancement of the assembly is terminated above a point 20 at the first bifurcation of trachea 16. As thus shown, the bend at distal end 76 of insertion sheath 72 is oriented toward left mainstem bronchus 28 leading into left lung 26 (not shown). When sampling catheter 62 is advanced out of distal end 76 of insertion sheath 72 with insertion sheath 72 disposed in the orientation illustrated in FIG. 4, then tip 74 of sampling catheter 62 advances into left mainstem bronchus 28 and ultimately into left lung 26 (not shown) of patient 10.

Nevertheless, due to the structure of insertion sheath 72 in particular, it is possible in the alternative, and with a high degree of reliability, to orient tip 74 of sampling catheter 62 into right mainstem bronchus 24, thereby to cause tip 74 ultimately to wedge into a bronchiole in right lung 22 (not shown) of patient 10. To accomplish this end, it is only necessary to rotate proximal end 80 (FIGS. 2 and 3) of insertion sheath 74 outside the body of patient 10. Because of the relative structural rigidity imparted to insertion sheath 72 by the material of which it is comprised, rotation of proximal end 80 thereof results in a one-to-one rotation of distal end 76 as, for example, illustrated by arrow R. Rotation of insertion sheath 72 about the longitudinal axis thereof in the manner illustrated by arrow R in FIG. 4 will eventually bring the bend at distal end 76 of insertion sheath 72 into the position shown in FIG. 4 in dashed lines, oriented toward right mainstem bronchus 24. The advancement of sampling catheter 62 (not shown) out of distal end 76 of insertion sheath 72 would then advance tip 74 of sampling catheter 62 into right mainstem bronchus 24.

Figure 4:
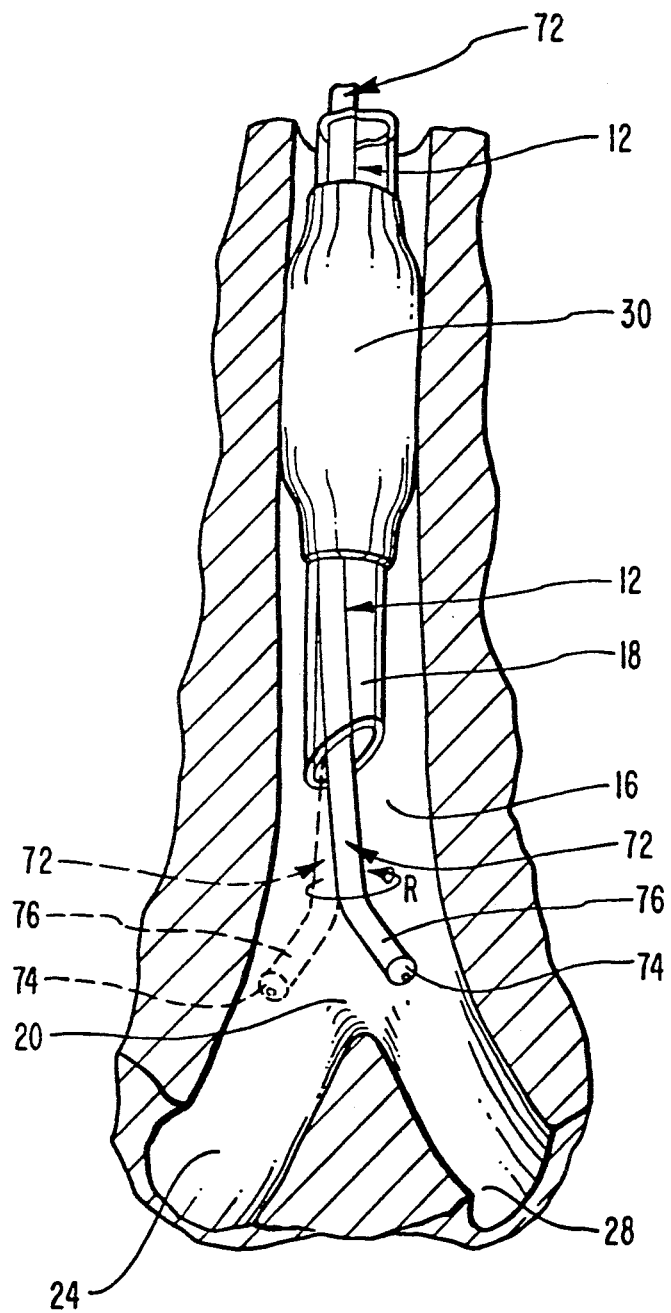
FIG. 4 is a schematic illustration of one step in the use of the bronchoalveolar lavage catheter of FIGS. 2 and 3, wherein the distal end of the sampling catheter is extended out of the distal end of an endotracheal tube.

Nevertheless, proceeding from the orientation of distal end 76 of insertion sheath 72 shown in FIG. 4 in solid lines, in order to insure that tip 74 of sampling catheter 62 (not shown) enters left lung 26, it is advisable to further advance the assembly of insertion sheath 72 and sampling catheter 62 into the body of patient 10. In this manner distal end 76 of insertion sheath 72 actually enters left mainstem bronchus 28 before sampling catheter 62 is advanced from distal end 76 thereof.

Until this point, tip 74 has effected a sealing engagement with distal end 76 of insertion sheath 72, whereby the outer surface of sampling catheter 62 has been protected from contamination of the type typically located in the upper respiratory system of a patient. Nevertheless, during the advancement process the outer surface of tip 74 of sampling catheter 62 may have become contaminated and aperture 85 communicating therethrough into the lumen (not shown) in sampling catheter 62 may have become blocked by a mucus plug. Accordingly, after full advancement of insertion sheath 72 into the body of patient 10, distal end 84 of sampling catheter 62 is advanced a short distance out of distal end 76 of insertion sheath 72 in the manner shown in FIG. 5, and a small quantity of sampling fluid 86 from reservoir 46 (FIG. 1) is used to flush any mucus plug from aperture 85 in tip 74.

In accordance with the inventive method for effecting and verifying correct wedging of tip 74 into a bronchiole 88 of patient 10, gas pressure monitor 50 is placed in communication through aperture 85 in tip 74 with the air passageways of patient 10 distal of distal end 84 of sampling catheter 62. This is accomplished, by first moving sampling stopcock 66 (FIG. 1) into a position blocking fluid flow from reservoir 46. Pressure stopcock 59 is then rotated to place the lumen in sampling catheter 62 in communication with gas pressure tubing 58. In this manner the pressure transducer in gas pressure monitor 50 is coupled to the proximal end of bronchoalveolar lavage catheter 60.

Pressure waveforms are generated from the pressure transducer that reflect changes in the air pressure in the body of the patient at the distal end of bronchoalveolar lavage catheter 60. The result is a baseline pressure waveform which can be used as a point of comparison with pressure waveforms subsequently acquired at distal end 84 of sampling catheter 62 as tip 74 interacts with the walls of bronchiole 88 of patient 10. As a result of this comparison, the nature of the interaction occurring can be verified with specificity.

Figure 6:
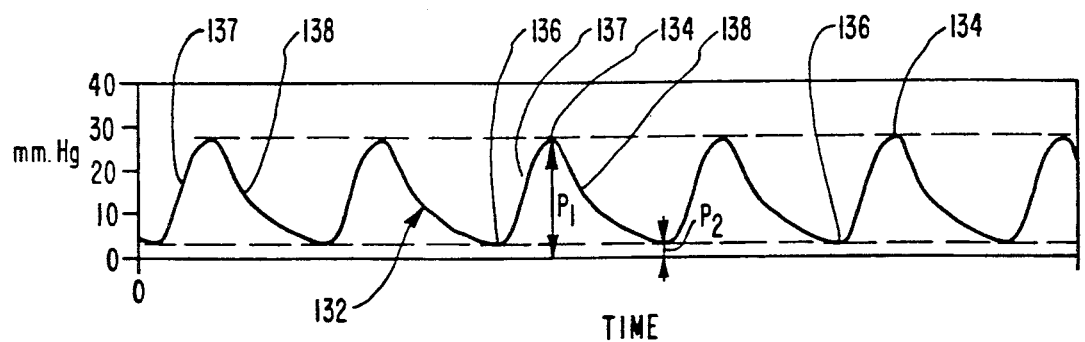
FIG. 6 is a graph of a typical baseline pressure waveform obtainable at the distal tip of the bronchoalveolar lavage catheter illustrated in FIG. 5.

A typical baseline pressure waveform 132 is shown in FIG. 6 derived from an experimental study conducted using a sheep. The sheep was infected with pneumonia, and bronchoalveolar lavage was conducted thereon through a tracheostomy tube. Other pressure waveforms appearing in the present disclosure resulted from the same study. In FIG. 6 and the other graphs included in the present disclosure, the vertical axis represents the air pressure distal of tip 74 of sampling catheter 62 inside the lung. The air pressure scale ranges from zero (0) to forty (40) millimeters of mercury. The horizontal axis represents time, so that the waveform illustrated is a real-time depiction of the air pressure variations being observed. The speed of the trace producing base line pressure waveform 132 was adjustable by the operator to accentuate characteristics anticipated to be indicative of distinct wedging-related conditions of interest to the operator.

Baseline pressure waveform 132 comprises a succession of waves in the form of a repeating sequence of high pressure peaks with intervening low, but positive, pressure troughs. Each wave has a high pressure peak 134 at a pressure $P_1$ and an intervening low pressure trough 136 at a positive pressure $P_2$. As shown in FIG. 6, pressure $P_1$ is in the range of from about twenty-two (22) to about twenty-eight (28) millimeters mercury, and more particularly in the range of from about twenty-five (25) to about twenty-seven (27) millimeters of mercury. On the other hand, low pressure troughs 136 occur at a pressure $P_2$ in the range of from about one (1) to about seven (7) millimeters of mercury, or more particularly in the range from about two (2) to about four (4) millimeters of mercury. Baseline pressure waveform 132 exhibits characteristic rapid upstrokes 137, terminating in rounded peaks 134 and relative steep, but flattening down strokes 138, terminating in almost flat low pressure troughs 136.

Pressure waveforms, such as baseline pressure waveform 132, are produced in a subject regardless of whether that subject is breathing naturally or is under mechanical ventilation. Naturally, in the latter circumstances, the features of baseline pressure waveform 132 should conform substantially to the established ventilating parameters set for the subject involved.

It should be understood that baseline pressure waveform 132 is only typical of the type of the baseline pressure waveform that might be derived by monitoring the air pressure in the air passageways of a patient. Thus, baseline pressure waveform 132 is not definitive, but should be viewed as illustrative only.

In addition, baseline pressure waveforms will vary among individuals. Thus a given baseline pressure waveform can only be used for purposes of comparison with subsequently acquired pressure waveforms for the same patient.

Figure 5:
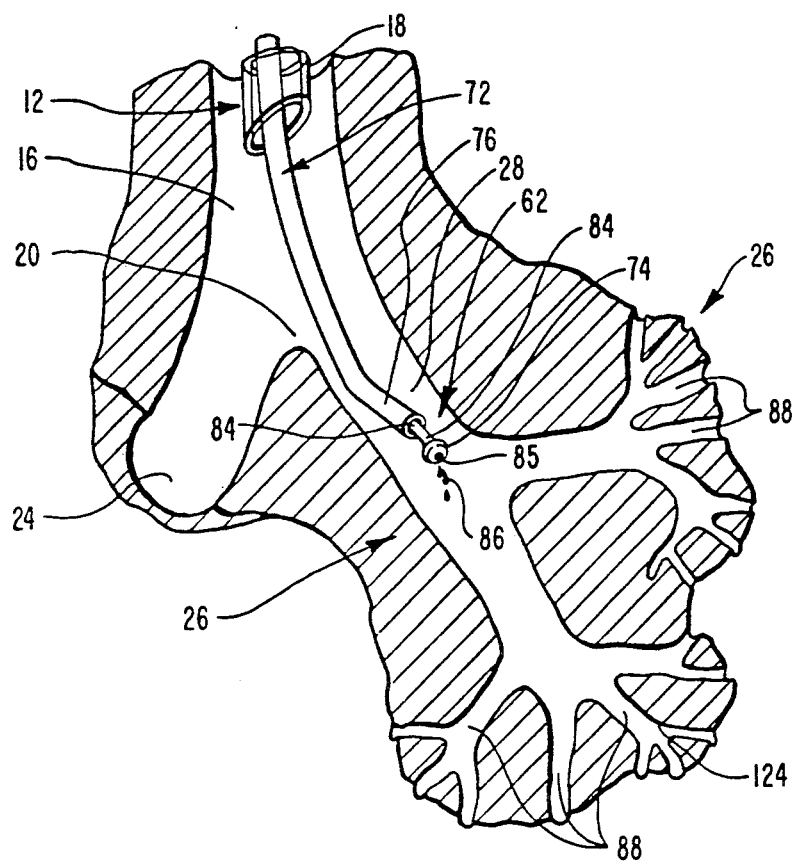
FIG. 5 is a schematic illustration of another step in the use of the bronchoalveolar lavage catheter of FIGS. 2 and 3, wherein the insertion sheath is extended into a preselected mainstem bronchus, and the distal end of the sampling catheter is extended out of the distal end of the sampling sheath.

Baseline pressure waveforms should be obtained after flushing aperture 85 with sampling fluid 86, as shown in FIG. 5, to ensure unobstructed communication between the pressure transducer in of gas pressure monitor 50 and the air passageways of a patient distal of bronchoalveolar lavage catheter tip 74. Once a baseline pressure waveform is obtained, inner sampling catheter 62 is advanced into patient 10 as the operator observes gas pressure monitor 50. This causes sampling catheter 62 to be advanced further out of insertion sheath 72 and into a bronchiole 88 of patient 10, until tip 74 of sampling catheter 62 encounters resistance to forward movement by interacting with the walls of bronchiole 88.

Such interactions, however, do no alone indicate that correct wedging has occurred. Instead, conditions of overwedging or ineffectual and precluded wedge may have been developed. Accordingly, as will be discussed below, wedging should be verified through the use of gas pressure monitor 50 prior to the infusion of sampling solution.

It is also frequently the case that the medical personnel operating bronchoalveolar lavage catheter 60 conclude without encountering tangible resistance to forward movement of bronchoalveolar lavage catheter 60 that wedging has occurred. Under such circumstances, according to the teachings of the present invention, correct wedging should also be verified through the use of gas monitor 50.

Once correct wedging has been verified, however, longitudinal movement of sampling catheter 62 is preferably restrained, for example, by the restraining means of bronchoalveolar lavage catheter access port 44 (FIG. 1). Thereafter sampling fluid from reservoir 46 is infused and withdrawn using sampling stopcock 66 in combination with syringe 48.

Baseline pressure waveform 132 is contrasted with subsequently acquired pressure waveforms to determine whether these acquired pressure waveforms exhibit characteristics corresponding to distinct wedging-related conditions of interest to medical personnel. These distinct wedging conditions include, not only conditions of correct wedging, but conditions of ineffective and precluded wedging in which infusion of sampling fluid would be inappropriate. Thus as bronchoalveolar lavage catheter 60 is advanced, inner sampling catheter 62 may encounter physical resistance without causing any concomitant change in pressure waveform being exhibited on air pressure monitor 50. Correct wedging would not exist under such conditions.

A second distinct wedging-related condition of interest occurs when the circumference of tip 74 of sampling catheter 62 makes full circumferential contact with the walls of a bronchiole 88, creating a correct wedging condition.

The third distinct wedging-related condition of interest in that of overwedging, wherein the circumference of distal tip 74 of inner sampling catheter 62 may contact with walls of a bronchiole 88, such that aperture 85 in tip 74 is in close proximity to a wall of bronchiole 88. In these conditions, normal respiration may result in drawing tissue of the walls of bronchiole 88 into aperture 85 blocking further aspiration. In this overwedged condition sampling fluid 86 may be infused into bronchiole 88, but will predictably be prevented from removal when the walls of the bronchiole 88 are drawn over aperture 85 by the suction required for aspiration. It is also possible to produce an overwedged condition when tissue from the walls of a bronchiole 88 directly enter aperture 85 due to the orientation of tip 74 as it engages those walls.

Figure 7A:
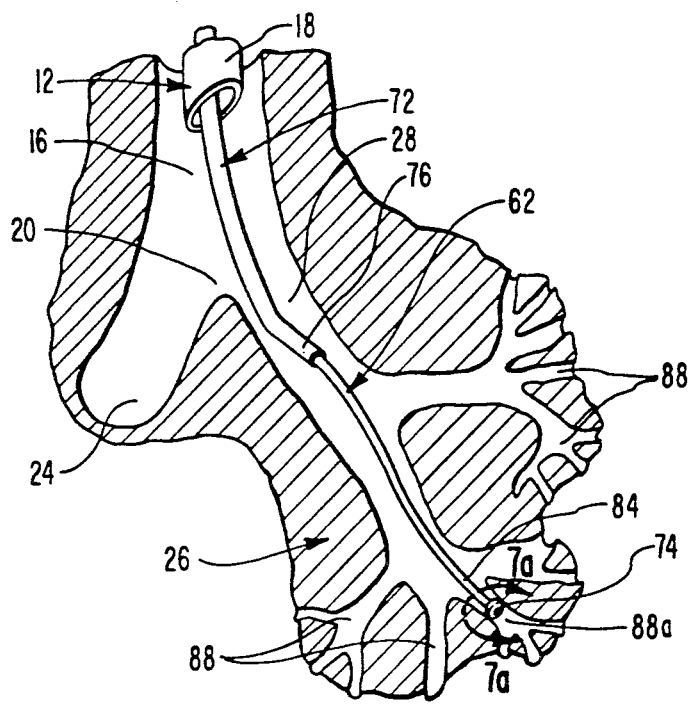
FIG. 7a is a schematic illustration of yet another step in the use of the bronchoalveolar lavage catheter of FIGS. 2 and 3, wherein the tip at the distal end thereof is correctly wedged in a bronchiole of a patient.

As indicated in FIG. 7a, distal end 84 of sampling catheter 62 is advanced out of insertion sheath 72 and along the air passages of patient 10 until tip 74 meets resistance to its advancement. In FIG. 7a and in the detail associated therewith in FIG. 7b, correct wedging of tip 74 in a bronchiole 88a is illustrated. There, the tissue of walls 139 of bronchiole 88a achieve secure contact about the full outer circumference 140 of tip 74. This contact seals the alveolar chamber distal of tip 74 into a closed space allowing sampling fluid 86 to be infused and aspirated into a controlled portion of the lung.

The creation of a closed system in this manner, tends to contain sampling fluid 86 in the alveolar chamber distal of tip 74 and enables efficient aspiration. Conditions of correct wedging also reduce the likelihood that infused sampling fluid will escape from the air passageways distal of tip 74, entering other portions of the lung from which the fluid cannot be removed.

Another manner of effecting correct wedging will be disclosed subsequently in relation to a second embodiment of a sampling catheter, such as sampling catheter 62.

Figure 7B:
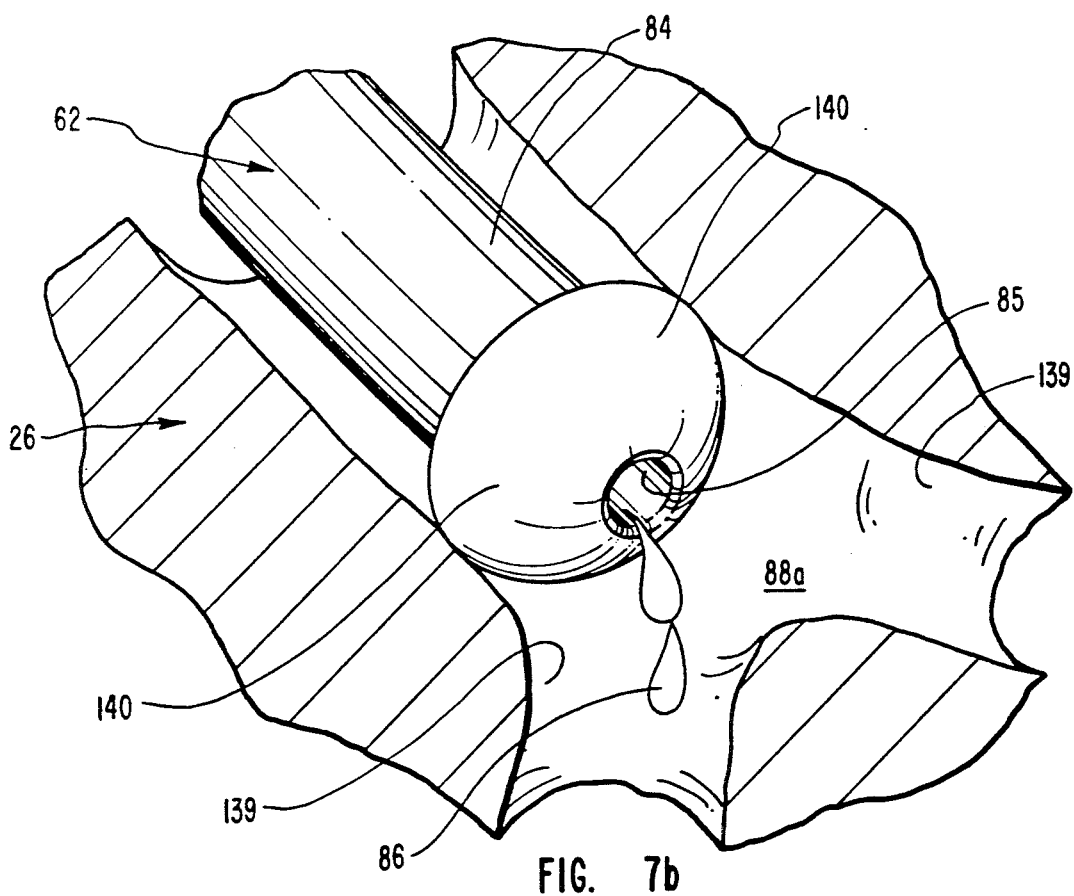
Figure 8A:
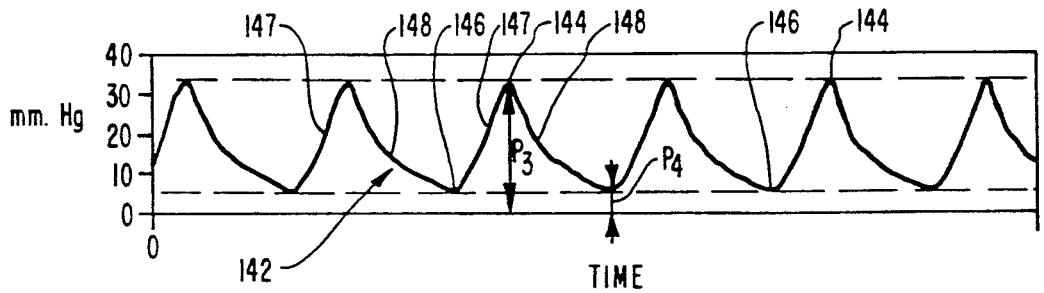
FIG. 8a is a first graph of a typical desired pressure waveform obtainable at the correctly wedged distal tip of the bronchoalveolar lavage catheter illustrated in FIGS. 7a and 7b.

FIG. 8a is a graph of a desired pressure waveform 142 obtained under conditions of correct wedging, such as those illustrated in FIG. 7b. Nevertheless, desired pressure waveform 142 is only typical of the type of desired pressure waveforms obtainable by monitoring the air pressure variations in the air passageways of a patient under conditions of correct wedging. Accordingly, desired pressure waveform 142 does not define the nature of all desired pressure waveform and should properly be viewed as illustrative only.

Desired pressure waveform 142 exhibits in a general sense the characteristics of a damped version of baseline waveform 132. Thus, desired pressure waveform 142 is a series of waves comprising a sequence of alternating high pressure peaks 144 at a pressure $P_3$ alternating with low, but positive, pressure troughs 146 at a pressure $P_4$. Pressure $P_3$ as shown in FIG. 8a is in the range of from about thirty (30) to about thirty-eight (38) millimeters of mercury, and more specifically, in the range from about thirty-one (31) to about thirty-four (34) millimeters of mercury. Pressure $P_4$ is in the range of from about two (2) to about eight (8) millimeters of mercury, and more particularly, in the range from about four (4) to about six (6) millimeters of mercury.

Desired pressure waveform 142 exhibits a more steeply sloped upstroke 147 than does baseline pressure waveform 132 of FIG. 6. Upstrokes 147 culminate at a higher pressure and in more pointed high pressure peaks 144 than the corresponding feature of baseline pressure waveforms 132. Downstroke 148 inclines downwardly following high pressure peak 144 in a less precipitous manner than does downstroke 138 of baseline pressure waveform 132. Compensatingly, however, downstroke 148 never assumes the flatness exhibited in the latter portion of downstroke 138. Low pressure trough 146, while at a somewhat elevated pressure from that of low pressure trough 136 in baseline pressure waveform 132, is more pointed than the corresponding feature of baseline pressure waveform 132.

FIG. 8a is a graph of a second desired pressure waveform 152 obtained under conditions of correct wedging, such as those illustrated in FIG. 7b. Nevertheless, desired pressure waveform 152 is but one example of the type of desired pressure waveform obtainable by monitoring the air pressure variations in the air passageways of a patient under conditions of correct wedging. Accordingly, the features of desired pressure waveform 152 are offered by way of example in the present disclosure, and not limitation.

Desired pressure waveform 152 also exhibits the characteristics of a damped version of baseline waveform 132. Thus, desired pressure waveform 156 is a series of waves comprising alternating high pressure peaks 154 and low pressure troughs 156 at pressures $P_5$ and $P_6$, respectively. Pressure $P_5$ is in the range from about twenty-eight (28) to about thirty-two (32) millimeters of mercury, or preferably the range from about twenty-nine (29) to about thirty-one (31) millimeters of mercury. Pressure $P_6$ L is in the range from about eight (8) to about twelve (12) millimeters mercury, or more preferably, in the range from about nine (9) to about eleven (11) millimeters mercury.

While desired waveform 152 maintains the periodicity apparent in baseline pressure waveform 132 in FIG. 6, characteristic deviations therefrom indicative of correct wedging are also apparent. The first is the generally elevated pressures $P_5$ and $P_6$ relative to pressures $P_1$ and $P_2$, respectively, of baseline pressure waveform 132. In addition, desired pressure waveform 152 exhibits an upstroke 157 that is steeper than the corresponding feature of baseline pressure waveform 132. Upstrokes 157 terminate in a relatively sharper high pressure peak 154 than high pressure peak 134 of baseline waveform 132. Downstroke 158 is shorter in the vertical direction than the corresponding feature of baseline pressure waveform 132, resulting in a flatter low pressure trough 156 than low pressure trough 136 thereof.

Figure 9A:
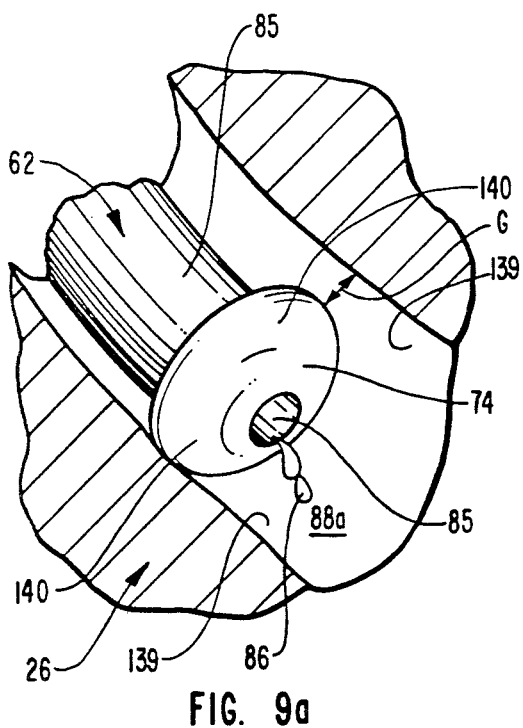
FIG. 9a is a schematic illustration of a condition of ineffective wedging of the distal tip of the bronchoalveolar lavage catheter illustrated in FIGS. 2 and 3.
Figure 9B:
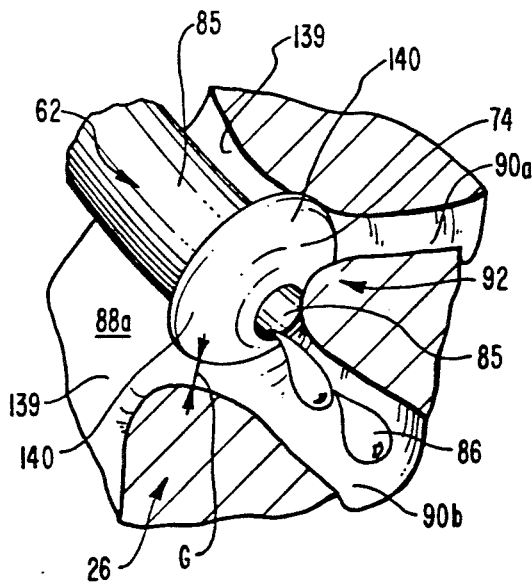
FIG. 9b is a schematic illustration of a condition of precluded wedging of the distal tip of the bronchoalveolar lavage catheter illustrated in FIGS. 2 and 3.

By contrast to the correct wedging illustrated in FIG. 7b, FIGS. 9a and 9b illustrate conditions under which tip 74 of sampling catheter 62 has been unable to effect correct wedging in a bronchiole 88a of left lung 26 of patient 10.

FIG. 9a illustrates conditions typical of ineffective wedging. While some portions of outer circumference 140 of tip 74 are engaged by the walls 139 of bronchiole 88a, a gap G remains at some points along outer circumference 140, so that the air passageways distal of tip 74 are not sealed off from the rest of the air passageways in lung 26. Accordingly, sampling fluid 86 infused through aperture 85 can escape through gap G into other portions of the lung 26 than the air passageways distal of tip 74. In addition, when aspiration is attempted, the existence of gap G prevents the establishment of the suction required to withdraw the infused sampling fluid 86 in air passageways distal of tip 74.

Conditions such as those in FIG. 9a arise in part due to irregular shaping or branching of bronchiole 88a, or the development therein of so substantial an amount of mucous as to give the operator a sense of physical resistance to advancement of tip 74 when conditions of correct wedging have not been effected. For whatever reason, the infusion of sampling fluid 86 under the conditions illustrated may produce health hazards to patient 10 and provide an inadequate sample volume.

FIG. 9b illustrates conditions typical of precluded wedging. Physical resistance may be encountered to advancement of tip 74, while still failing to result in conditions of correct wedging. As seen in FIG. 9b, the advancement of sampling catheter 62 into bronchiole 88a has brought tip 74 into proximity of the branching of bronchiole 88a into sub-bronchioles 90a and 90b. Instead of entering one of sub-bronchioles 90a or 90b, tip 74 has become lodged against the tissue 92 disposed therebetween. Resistance to the advancement of sampling catheter 62 will be felt by the operator, but as seen in FIG. 9b, the full circumference 194 of tip 74 is not engaged by the walls 139 of bronchiole 88a. Neither is aperture 85 in tip 74 blocked by tissue 92. Accordingly, sampling fluid 86 infused through aperture 85 will pass into sub-bronchiole 90b, but because of the gap G between a portion of outer circumference 140 of tip 74 and walls 139 of bronchiole 88a, sampling fluid 86 can escape from the air passageways distal of tip 74. In addition, when aspiration is attempted, the existence of gap G prevents the development of sufficient suction for removing sampling fluid 86 from sub-bronchiole 90b.

The conditions illustrated in FIG. 9a of ineffective wedging or in FIG. 9b of precluded wedging do not isolate the air passageways distal of tip 74 from the rest of the air passageways in the lung of the patient. Air pressure changes in the air passageways distal of tip 74 correspond to air pressure changes resulting from the ventilation of patient 10, whether that ventilation is undertaken with or without mechanical assistance. The air pressure waveforms resulting under conditions such as those illustrated in FIGS. 9a and 9b are thus substantially similar to baseline pressure waveform 132 of FIG. 6.

Through the use of air pressure monitor 50, an operator is provided with information indicating that no infusion of sampling fluid 86 should be undertaken, as no correct wedging has been effected. This determination can be made by the operator through a visual inspection of the air pressure waveforms generated. If a comparison of these pressure waveforms with baseline pressure waveform 132 is undertaken on an automated basis, other means, such as the illumination of one of indicator lights 55 (FIG. 1), or the production of an audible tone 56, can be used to signal the operator that correct wedging has not been effected.

Figure 10A:
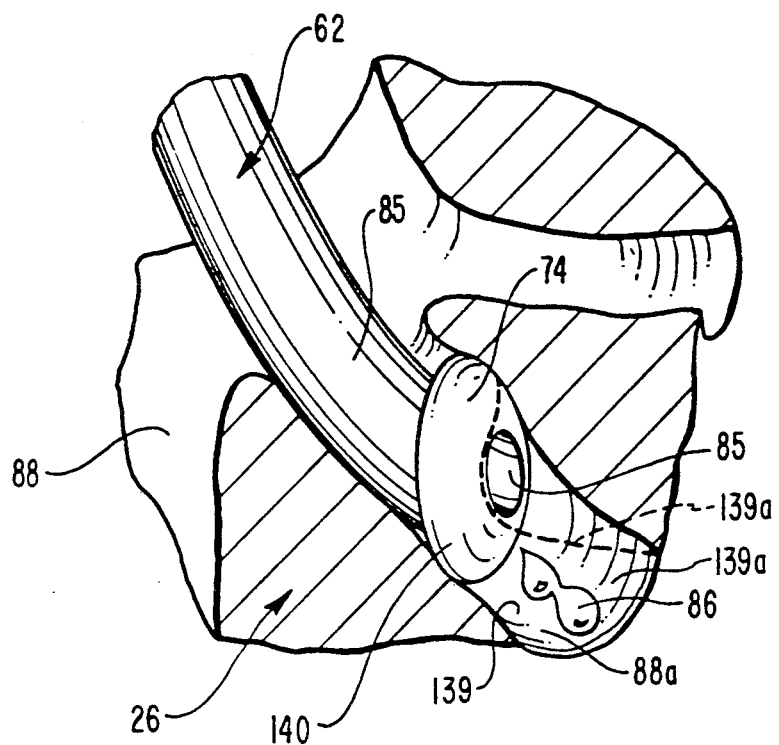
FIG. 10a is a schematic illustration of a condition of overwedging of the distal tip of the bronchoalveolar lavage catheter illustrated in FIGS. 2 and 3.
Figure 10B:
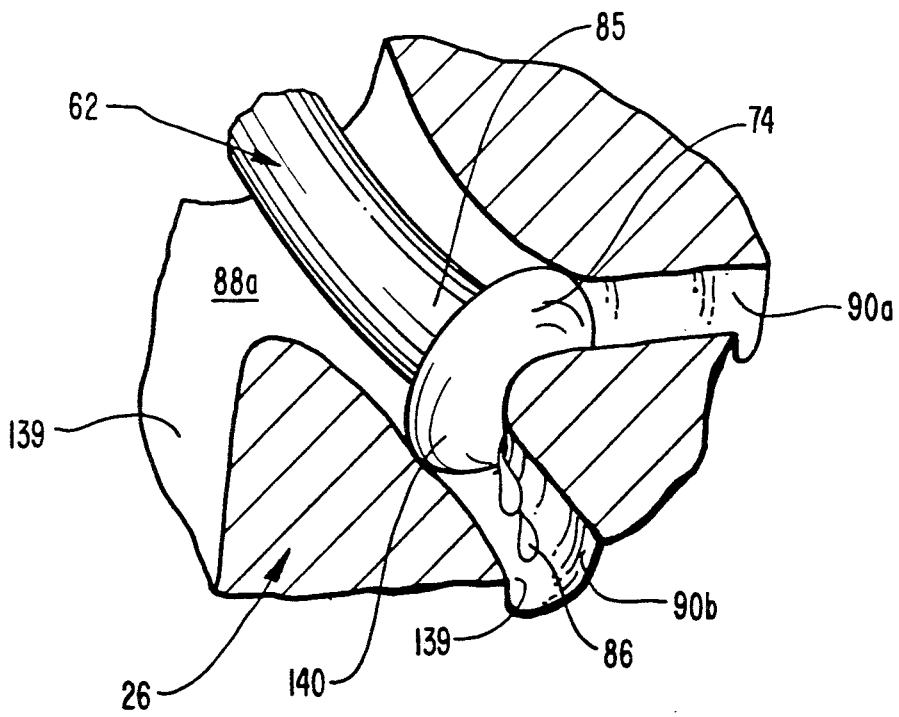
FIG. 10b is a second schematic illustration of a condition of overwedging by the distal tip of the bronchoalveolar lavage catheter illustrated in FIGS. 2 and 3.

FIGS. 10a and 10b illustrate circumstances which can give rise to overwedging of tip 76 in a bronchiole 88a of patient 10.

FIG. 10a illustrates an overwedged condition which occurs when distal tip 74 of sampling catheter 62 lodges in a bronchiole 88a at such an angle that aperture 85 thereof is not centrally located within bronchiole 88a. Rather, aperture 85 is proximate to one wall 139a of bronchiole 88a. Being relatively free of structural rigidity, wall 139a of bronchiole 88a can be drawn toward and into aperture 85 by normal respiration of patient 10. Under such conditions, it is predictable that any subsequent aspiration of any infused sampling fluid 86 cannot be effected. Such a situation is illustrated in FIG. 10a in dashed lines.

Under such conditions, sampling fluid 85 can be infused into the air passageways distal of tip 76, but because of the relatively flexible structure of the air passageways at the level of branching illustrated, it is highly likely that suction applied through sampling catheter 62 to those air passageways will distort the wall 139a of bronchiole 88a from the position shown in solid to the position shown in dashed lines. Then, the tissue of wall 139a will block aperture 85, precluding further aspiration of sampling fluid 85 from the air passageways distal of tip 76. This can result in health hazards to patient 10 and provide an inadequate sample volume. One advantage of the present invention is the capacity to detect such an overwedged condition prior to infusing irretrievable sampling fluid 85.

FIG. 10b illustrates another circumstance in which overwedging of tip 76 can occur. As shown, tip 74 of sampling catheter 62 has advanced into proximity with the branching of bronchiole 88a into sub-bronchioles 90a and 90b. Tip 74 has been driven head-on into the tissue 92 between sub-bronchioles 90a and 90b, so that tissue 92 blocks aperture 85 (not shown) in tip 74. Under such circumstances, whether or not outer circumference 140 of tip 74 engages walls 139 of bronchiole 88a, sampling fluid 85 can be infused into the air passageways distal of tip 74. Nevertheless, the interposition of tissue 92 into aperture 85 precludes the aspiration of any such infused sampling fluid 85.

Fortunately, according to the teachings of the present invention, an overwedged condition, such as that illustrated in FIGS. 10a or 10b, can be detected through the use of gas pressure monitor 150, before the infusion of any sampling fluid 85. Accordingly, although resistance would be experienced by, an operator to the further advancement of sampling catheter 62 into left lung 26 of patient 10, the operator could from the pressure waveforms generated determine that tip 74 should be withdrawn slightly with sampling catheter 62 in order to again attempt a correct wedge therewith.

Figure 11A:
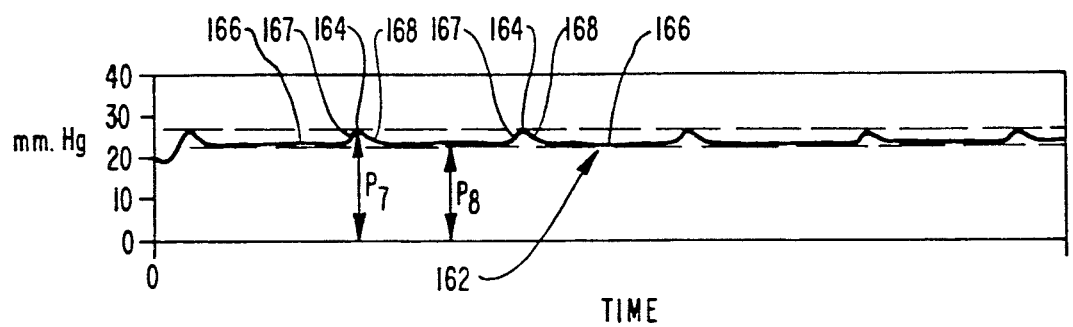
FIG. 11a is a first graph of a typical overwedged pressure waveform obtainable at the overwedged distal tip of the bronchoalveolar lavage catheter illustrated in FIGS. 10a and 10b.
Figure 11B:
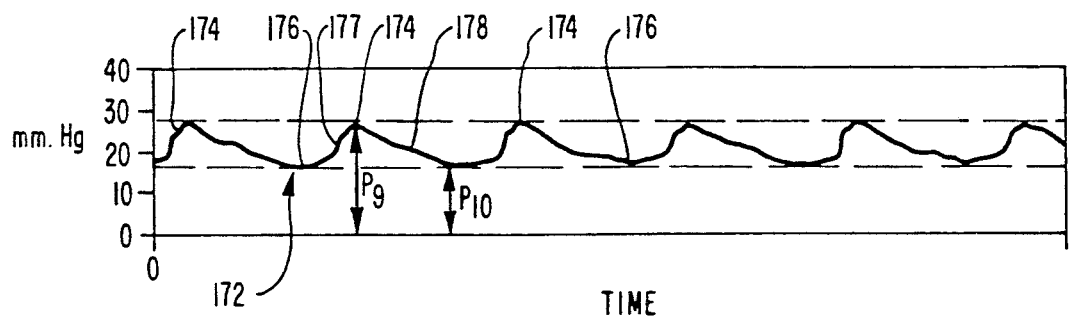
FIG. 11b is a second graph of a typical overwedged pressure waveform obtainable at the overwedqed distal tip of the bronchoalveolar lavaqe catheter illustrated in FIGS. 10a and 10b.
Figure 11C:
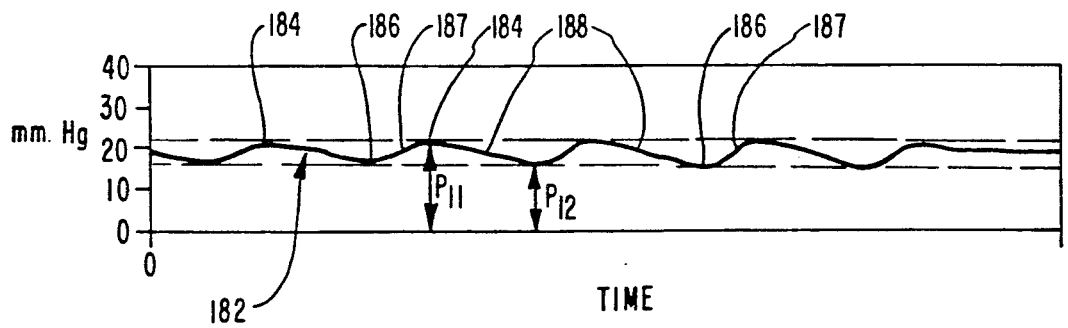
FIG. 11c is a third graph of an overwedged pressure waveform obtainable at the distal tip of the bronchoalveolar lavage catheter illustrated in FIGS. 10a and 10b.

The nature of the pressure waveforms generated in overwedged conditions will be explored in relation to the graphs depicted in FIGS. 11a through 11c. When such overwedged pressure waveforms are detected by medical personnel, inner sampling catheter 62 can be slightly retracted, rotated, and then readvanced in order to renew the effort to effect correct wedging.

FIG. 11a is a graph of an overwedged pressure waveform 162 obtained under conditions of overwedging, such as are illustrated in FIG. 10a and 10b. Nevertheless, overwedged pressure waveform 162 is only illustrative of the type of waveform obtained when air pressure variations in the air passageways of a patient are monitored under conditions of overwedging. Accordingly, the features of overwedged pressure waveform 162 can properly be viewed only as exemplary, rather than as limitative.

Overwedged pressure waveform 162 exhibits in a general sense the characteristics of an overly-damped version of baseline waveform 132 shown in FIG. 6. Thus, overwedged pressure waveform 162 is a series of waves comprising a succession of alternating high pressure peaks 164 at a pressure $P_7$ and low, but positive, pressure troughs 166 at a pressure $P_8$. Pressure $P_7$ as shown in FIG. 11a is in the range of from about twenty-three (23) to about twenty-eight (28) millimeters of mercury, or more specifically, in the range from about twenty-four (24) to about twenty-six (26) millimeters of mercury. Pressure $P_8$ is in the range of from about twenty (20) to about twenty-four (24) millimeters mercury, or more particularly in the range of from about twenty-two (22) to about twenty-three (23) millimeters of mercury.

Overwedged pressure waveform 162 exhibits severe and abrupt flattening in the area of low pressure troughs 166, which is characteristic of over-damped pressure waveform corresponding to an overwedged condition. The relatively minor pressure differences between pressure $P_7$ of high pressure peaks 164 and pressure $P_8$ of low pressure troughs 166 is further indicative of a condition in which virtually no pressure variation is observable between inhalation and exhalation in the air passageways distal of tip 74. At most, overwedged pressure waveform 162 resembles base line pressure waveform 132 of FIG. 6 only in the periodicity of high pressure peaks 164. Otherwise, the qualities of upstrokes 167 and downstrokes 168 of overwedged pressure waveform 162 are hardly characterizable, given the shortness of the lengths thereof. Overwedged pressure waveform 162 is dominated by the flattening of downstroke 168 into lengthy troughs 166 corresponding to low pressures $P_8$ substantially elevated relative to low pressure $P_2$ of base line pressure waveform 132 Under some circumstances of severe overwedging, the pressure waveform resulting may flatten entirely, so that no periodicity whatsoever is detectable. Overwedged waveform 162 might be expected in conditions of overwedging such as those illustrated in FIG. 10b, where tissue blocks aperture 85 (not shown) at all times, rather than intermittently, as shown in FIG. 10a.

Illustrated in FIG. 11b is a second overwedged pressure waveform 172 reflecting overwedged conditions, such as those illustrated in FIGS. 10a or 10b. It should be born in mind that overwedged pressure waveform 172 is only typical of the type of waveform produced when air pressure variations in the air passageways of a patient are monitored under conditions of overwedging. The features of overwedged pressure waveform 172 are accordingly disclosed herein for the purpose of example, rather than limitation.

Overwedged pressure waveform 172 is a less severely overdamped version of base line pressure waveform 132 than is overwedged pressure waveform 162 of FIG. 11a. Overwedged pressure waveform 172 is a series of waves comprising a succession of alternating high pressure peaks 174 at a pressure $P_9$ and low, but positive, pressure, troughs 176 at a pressure $P_{10}$. As seen in FIG. 11b, pressure $P_9$ is in the range of from about twenty-four (24) to about thirty (30) millimeters of mercury, or more preferably, in the range from about twenty-five (25) to about twenty-eight (28) millimeters of mercury.

Overwedged pressure waveform 172 exhibits irregular upstrokes 177 terminating in rounded high pressure peaks 174. Long gradually sloping downstrokes 178 lead to round, almost flat low pressure troughs 176. Minor pressure differential exist between pressure $P_9$ of high pressure peaks 174 and pressure $P_{10}$ of low pressure troughs 176 thus tends to suggest that, for at least a portion of each cycle of inhalation and exhalation, aperture 85 is totally or partially blocked by some structure, such as the tissue of a wall of a bronchiole.

Illustrated in FIG. 11c is a third overwedged pressure waveform 182 reflecting conditions such as those illustrated in FIGS. 10a or 10b. Overwedged pressure waveform 182 is, however, only exemplary of the type of waveform that is produced when the air pressure variations in air passageways of a patient are monitored in conditions of overwedging. The features of overwedged pressure waveform 182 are, accordingly, offered herein for the purpose of example, rather than limitation.

Overwedged pressure platform 182 exhibits a degree of over-damping intermediate that of overwedged pressure waveform 162 of FIG. 11a and overwedged pressure waveform 172 of FIG. 11b. Overwedged pressure waveform 182 comprises a series of waves taking the form of a succession of alternating high pressure peaks 184 at a pressure $P_{11}$ and low, but positive, pressure troughs 186 having a pressure $P_{12}$. As seen in FIG. 11c, pressure $P_{11}$ is in the range of from about nineteen (19) to about twenty-five (25) millimeters of mercury, or more specifically, from about twenty-one (21) to about twenty-three (23) millimeters of mercury. Pressure $P_{12}$ is in the range of from about fifteen (15) to about twenty (20) millimeters of mercury, or more particularly in the range from about seventeen (17) to about nineteen (19) millimeters of mercury.

Overwedged pressure waveform 182 exhibits rolling high pressure peaks 184 and low pressure troughs 186, both well rounded and interconnected by relatively linear upstrokes 187 and downstrokes 188. Nevertheless, in an overall sense, when compared to baseline pressure waveform 132 of FIG. 6, overwedged pressure waveform 182 is severely flat in terms of the extremes of its high and low pressures, $P_{11}$ and $P_{12}$, respectively. This type of narrowing of the range of value found in a pressure waveform is taken to be indicative of an overwedged condition.

In some instances, it may be desirable to conduct bronchoalveolar lavage of a larger portion of a preselected lung of patient 10 than would be possible in the air passageways distal of the point at which tip 74 can effect a condition of correct wedging on a bronchiole. Toward this end, modifications can be made at distal end 84 of sampling catheter 62 which will permit the effecting of conditions of correct wedging in bronchioles of patient 10 having a diameter larger than the diameter of tip 74.

Figure 12A:
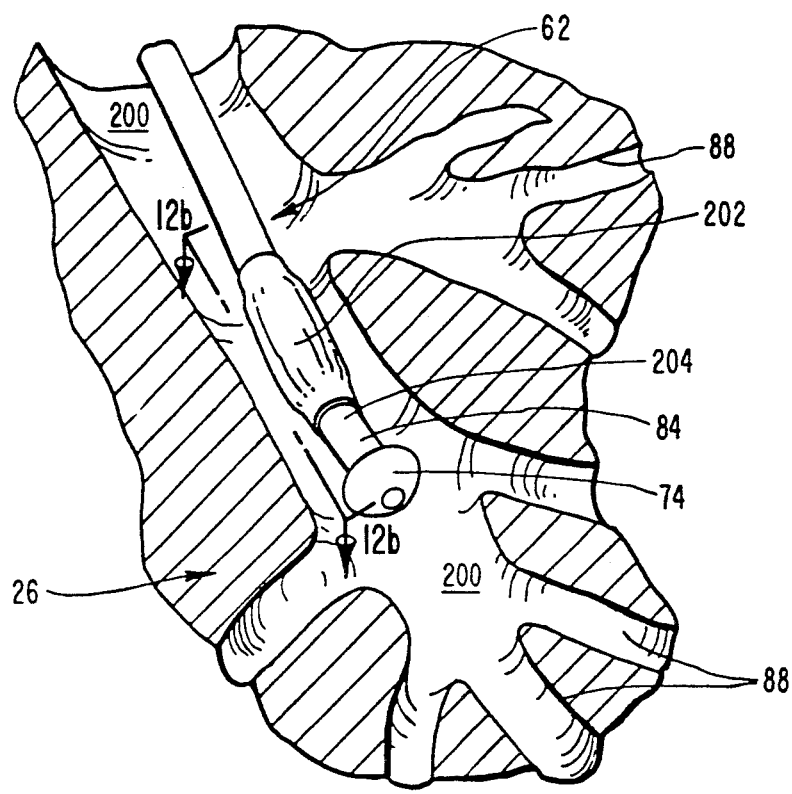
FIG. 12a is a schematic illustration of a second embodiment of the distal tip of the sampling catheter of the bronchoalveolar lavage catheter illustrated in FIGS. 2 and 3, having an inflatable cuff located on the exterior surface thereof.
Figure 12B:
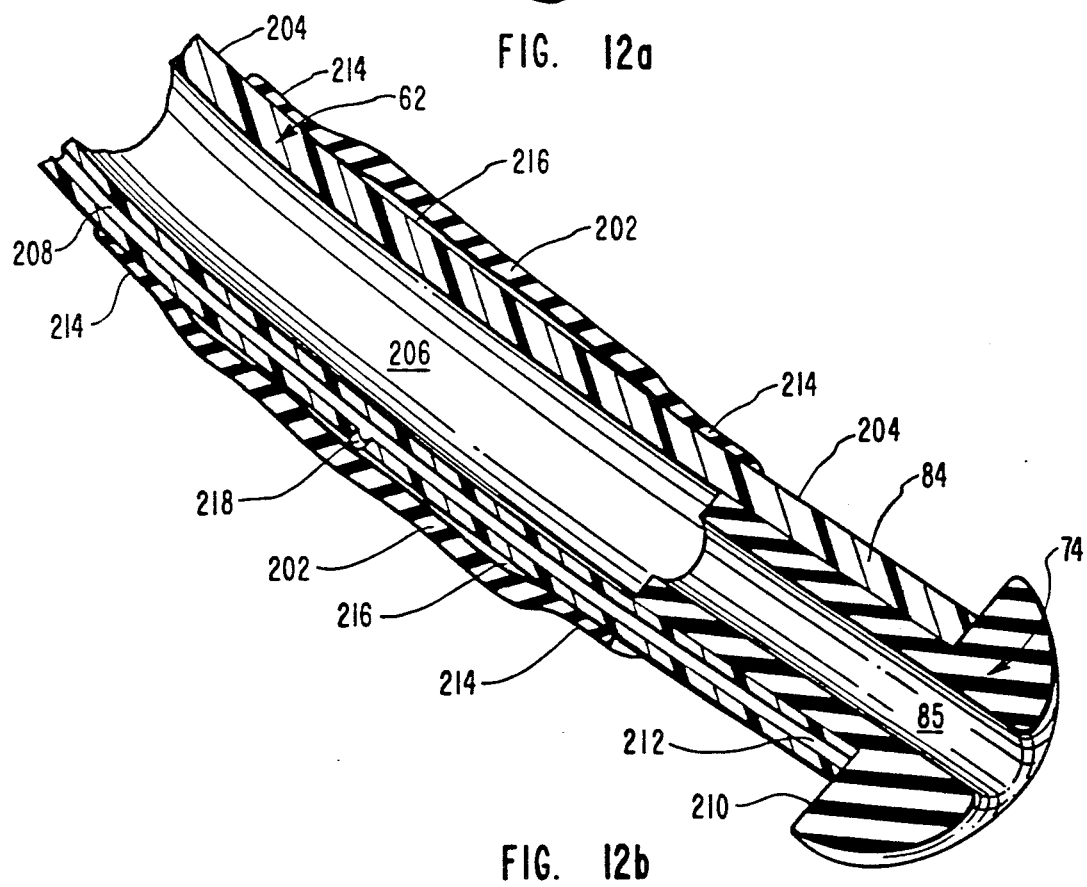
FIG. 12b is a cross-sectional view of the tip of the bronchoalveolar lavage catheter illustrated in FIG. 12a taken along section lines 12b-12b shown therein.

Accordingly, as seen in FIG. 12a, distal end 84 of sampling catheter 62 is shown disposed in a larger bronciole 100 of patient 10. In order to effect correct wedging in larger bronchiole 200, a flexible cuff 202 is attached to and encircles the outer surface 204 of sampling catheter 62 at a point proximal of tip 74. As more clearly understood by reference to the cross-sectional view found in FIG. 12b, sampling catheter 62 comprises a first lumen 206 so sized as to permit the infusion and aspiration of sampling fluid from reservoir 46. In addition, however, sampling catheter 62 comprises a second lumen 208 having a size relatively smaller than that of first lumen 206 and being capable of transmitting a gas from proximal end 64 of sampling catheter 62 to distal end 84 thereof. Tip 74 of sampling catheter 62 is secured in the end of first lumen 106 in such a manner that the proximal surface 210 of tip 74 closes distal end 212 of second lumen 208.

Flexible cuff 202 is a generally cylindrical structure which is secured at each periphery 214 thereof to outer surface 204 of sampling catheter 62, thereby defining between flexible cuff 202 and outer surface 204 an annular inflation space 216. An inflation aperture 218 communicates between second lumen 208 and inflation space 216. Flexible cuff 202 is thus inflated utilizing pressurized air from second lumen 108.

Figure 13:
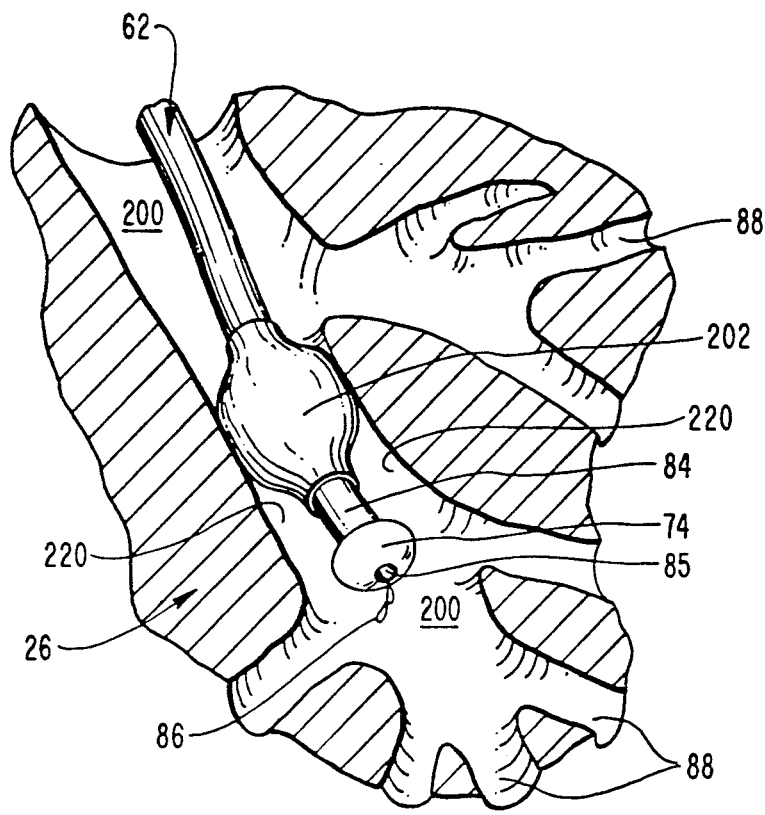
FIG. 13 is a schematic illustration of a condition of correct wedging of the distal tip of the bronchoalveolar lavage catheter illustrated in FIGS. 12a and 12b.

As illustrated in FIG. 13, the inflation of flexible cuff 202 brings it into engagement with the walls 220 of larger bronchiole 200 of patient 10, making a full circumferential seal therewith. Larger bronciole 200 has a diameter greater than that of the bronchiole in which tip 74 of sampling catheter 62 could otherwise become lodged directly, as in FIG. 7b.

Figure 8B:
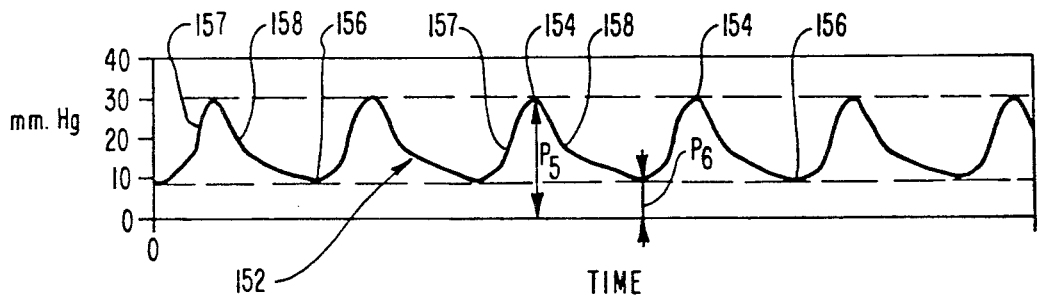
FIG. 8b is a second graph of a typical desired pressure waveform obtainable at the correctly wedged distal tip of the bronchoalveolar lavage catheter illustrated in FIGS. 7a and 7b.

In this manner, the air passageways of patient 100 distal of flexible cuff 202 and of tip 74 are isolated from the balance of the air passageways in left lung 26. Accordingly, the inflation of flexible cuff 202 has resulted in conditions of correct wedging, and sampling fluid 86 infused through aperture 85 can reliably be aspirated. Air pressure monitor 50 (FIG. 1) would, accordingly, exhibit an air pressure waveform such as a desired pressure waveform 152 in FIG. 8b indicative of correct wedging. A larger section of a preselected one of lungs of patient 10 can be subjected to bronchoalveolar lavage sampling.

Naturally, as with the earlier described embodiment of sampling catheter 62 which lacked any structure, such as flexible cuff 202, conditions of ineffective wedging, precluded wedging, and over-wedging can result in the manners as illustrated in FIGS. 9a, 9b, 10a, and 10b. In addition, however, certain specific conditions can develop with a sampling catheter provided with a flexible cuff, such as flexible cuff 202.

Figure 14:
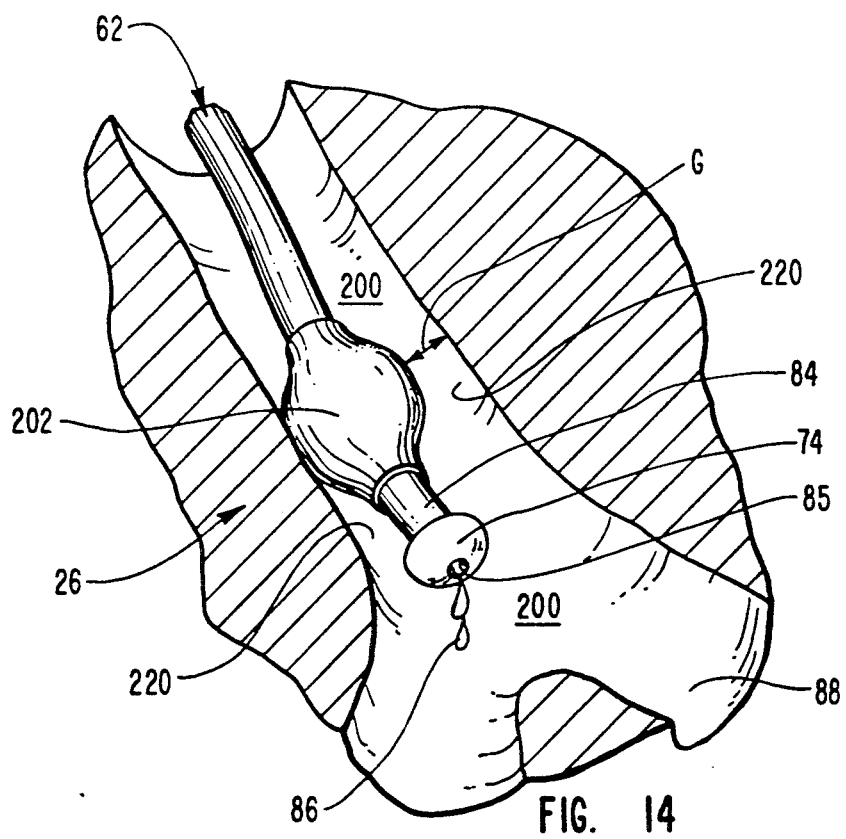
FIG. 14 is a schematic illustration of a condition of ineffective wedging of the distal tip of the bronchoalveolar lavage catheter illustrated in FIGS. 12a and 12b.

As shown in FIG. 14, for example, the under-inflation of flexible cuff 202 in larger bronchiole 200 may not result in a complete circumferential seal between walls 220 of larger bronchiole 200 and the outer most circumference of inflated flexible cuff 202. Accordingly, a gap G is shown between a portion of the outer circumference of flexible cuff 202 and the wall 220 of larger bronchiole 200. Through gap G sampling fluid 86 can escape from the air passageways distal of the flexible cuff 202. In addition, gap G precludes the application through aperture 85 of suction by which to recover infused sampling fluid 86. Under conditions illustrated in FIG. 14, a pressure waveform, such as baseline pressure waveform 132 of FIG. 6 would be observed, and an operator would be well advised to refrain from undertaking any infusion whatsoever. Instead, sampling catheter 62 could be advanced further into the air passageways of patient 10 or flexible cuff 202 could be additionally inflated.

Figure 15:
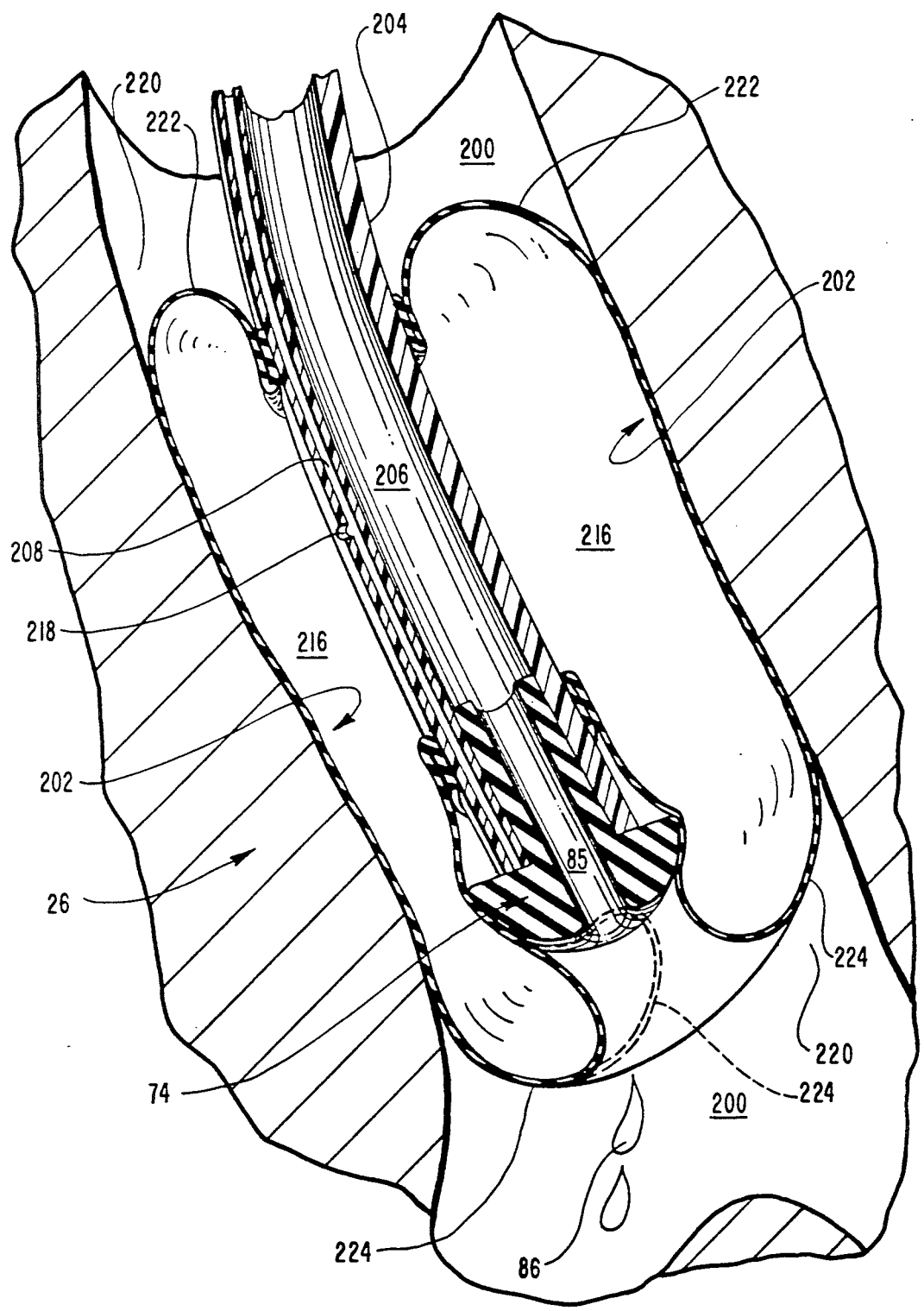
FIG. 15 is a schematic illustration of a condition of overwedging of the distal tip of the bronchoalveolar lavage catheter illustrated in FIGS. 12a and 12b.

Continued inflation of flexible cuff 202 beyond that required to effect a full circumferential seal against the walls of a given bronchiole, can also produce difficulties. As shown in FIG. 15, for example, over-inflation of flexible cuff 202 can cause portions of flexible cuff 202 to expand longitudinally along sampling catheter 62 within larger bronchiole 200. Thus, a first portion 222 of flexible cuff 202 has expanded along larger bronchiole 200 in the direction proximal of tip 74, while a second portion 224 of flexible cuff 202 has expanded longitudinally along larger bronchiole 200 to reach a position distal of tip 74.

Under such conditions, an effective wedging seal has been created, and sampling fluid 86 could conceivably be infused. Nevertheless, the presence of second portion 224 of flexible cuff 202 distal of tip 74 and of aperture 85 thereof is problematic. As shown in dashed lines in FIG. 15, the action of normal respiration by patient 10 is likely to draw the second portion of 224 of flexible cuff 202 toward and into aperture 85, predictably blocking any aspiration of infused sampling fluid 86. Accordingly, a condition of over-wedging would exist.

The relationship depicted in FIG. 15 would be reflected, however, in a pressure waveform 53 appearing on air pressure monitor 50 similar to over-wedging pressure waveform 162, 172, or 182 of FIGS. 11a, 11b, or 11c, respectively. The characteristics of and condition of over-wedging would then stimulate the operator to reduce the pressure in inflatable cuff 202 to see whether, on the basis of new air pressure waveforms, a condition of correct wedging could be effected. Ultimately, it may be necessary to totally deflate flexible cuff 202 and commence inflation again in gradual stages and at a new location in the bronchioles of patient 10.

It will be appreciated that the present invention provides a method and system for conveying to an operator the conditions existing at the distal tip of a bronchoalveolar lavage catheter in a manner that improves the accuracy of diagnostic efforts without resorting to costly bronchoscopic techniques. Through the use of the present invention, correct wedging must be confirmed before sampling fluid is infused, thereby alleviating the added burden on a patient of absorbing sampling fluid improperly infused into the lung thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A method for effecting wedging of the distal tip of a bronchoalveolar lavage catheter in a bronchiole in a lung of a patient, said method comprising the steps of:
 (a) coupling a pressure transducer to the proximal end of the lumen of the bronchoalveolar lavage catheter;

(b) advancing the bronchoalveolar lavage catheter in the air passageways of the patient;

(c) generating from the pressure transducer pressure waveforms reflective of air pressure variations in the air passageways of the patient distal of the tip of the bronchoalveolar lavage catheter;

(d) monitoring said pressure waveforms to detect therefrom the existence at the tip of the bronchoalveolar lavage catheter of significant wedging-related conditions of interest to medical personnel attempting to effect wedging of the distal tip of the bronchoalveolar lavage catheter; and (e) manipulating the proximal end of the bronchoalveolar lavage catheter on the basis of said predetermined wedging-related conditions detected in said step of monitoring.

2. A method as recited in claim 1, wherein said significant wedging-related conditions comprise:
   (a) a condition of correct wedging;
   (b) a condition of ineffectual wedging;
   (c) a condition of precluded wedging; and
   (d) a condition of overwedging.

3. A method as recited in claim 2, wherein said step of manipulating comprises the steps of:
   (a) ceasing said step of advancing when physical resistance rises thereto in the air passageways of the patient; and
   (b) fixing the longitudinal position of the bronchoalveolar lavage catheter, if said pressure waveform produced in said step of generating discloses the existence of conditions of correct wedging.

4. A method as recited in claim 2, wherein said step of manipulating comprises the steps of:
   (a) ceasing the step of advancing when a condition of correct wedging is suspected; and
   (b) fixing the longitudinal position of the bronchoalveolar lavage catheter, if said pressure waveform produced in said step of generating disclosures the existence of conditions of correct wedging.

5. A method as recited in claim 31, wherein said step of manipulating further comprises the step of readvancing the bronchoalveolar lavage catheter into the air passageways of the patient, if said air pressure waveforms indicate the existence of conditions of ineffectual wedging.

6. A method as recited in claim 2, wherein, if said step of monitoring discloses the existence of conditions of ineffectual wedging, precluded wedging, or overwedging, then said step of manipulating comprises the steps of:
   (a) partially withdrawing the bronchoalveolar lavage catheter;
   (b) rotating the bronchoalveolar lavage catheter; and
   (c) readvancing the bronchoalveolar lavage catheter in the air passageways of the patient.

7. A method as recited in claim 6, wherein said step of manipulating further comprises the step of fixing the longitudinal position of the bronchoalveolar lavage catheter relative to the body of the patient when a condition of correct wedging is detected in said step of monitoring.

8. A method for as recited in claim 1, said step of monitoring comprising the steps of:
   (a) developing a baseline pressure waveform for the patient reflecting air pressure variations in the air passageways of the patient distal of the tip of the bronchoalveolar lavage catheter due to ongoing, unobstructed ventilation of the patient; and
   (b) comparing said baseline pressure waveform with pressure waveforms developed as the tip of the bronchoalveolar lavage catheter is advanced in the air passageways of the patient to detect characteristics in said pressure waveforms associated with each of said significant wedging-related conditions.

9. A method as recited in claim 8, wherein said baseline pressure waveform comprises a recurrent series of waves.

10. A method as recited in claim 8, wherein said baseline pressure waveform comprises a recurrent series of alternating peaks and troughs.

11. A method as recited in claim 10, wherein said peaks correspond to high pressure peaks in the air pressure in the air passageways of the patient distal of the tip of the bronchoalveolar lavage catheter during ongoing, unobstructed ventilation of the patient.

12. A method as recited in claim 10, wherein said troughs correspond to low pressure troughs in the air pressure in the air passageways of the patient distal of the tip of the bronchoalveolar lavage catheter during ongoing, unobstructed ventilation of the patient.

13. A method as recited in claim 8, wherein said ventilation of the patient comprises natural breathing by the patient.

14. A method as recited in claim 8, wherein said ventilation of the patient comprises mechanical ventilation of the patient.

15. A method as recited in claim 1, wherein said step of coupling comprises the steps of:
   (a) securing a coupling adapter to the proximal end of the bronchoalveolar lavage catheter; and
   (b) interconnecting an air pressure tube between said coupling adapter and said pressure transducer.

16. A method as recited in claim 15, wherein said coupling adapter comprises a pressure stopcock capable of selectively placing said air pressure tube in communication with the lumen of the bronchoalveolar lavage catheter.

17. A method as recited in claim 1, wherein said step of coupling comprises the steps of:
   (a) placing a pressure stopcock in communication with the proximal end of the lumen of the bronchoalveolar lavage catheter;
   (b) securing to said pressure stopcock means for infusing and aspirating fluid through said bronchoalveolar lavage catheter; and
   (c) securing to said pressure stopcock an air pressure tube coupled to said pressure transducer, said pressure stopcock being capable of selectively placing said proximal end of the lumen of the bronchoalveolar lavage catheter in communication alternatively with said air pressure tube or with said means for infusing and aspirating.

18. A method as recited in claim 17, wherein said step of coupling further comprises the step of operating said pressure stopcock to place said air pressure tube in communication with the bronchoalveolar lavage catheter.

19. A method as recited in claim 1, wherein said step of generating comprises the step of making electrical connection between said pressure transducer and an air pressure monitor.

20. A method as recited in claim 19, wherein said pressure waveforms are presented in real time visually apprehendable form on said air pressure monitor.

21. A method as recited in claim 20, wherein said pressure waveforms are presented on a cathode ray tube.

22. A method as recited in claim 20, wherein said pressure waveforms are presented on a printout.

23. A method as recited in claim 19, wherein said step of monitoring comprises the step of performing computerized analysis of said pressure waveforms.

24. A method as recited in claim 19, wherein said step of generating further comprises the step of producing at said monitor an indication of the significant wedging-related condition in existence at the tip of the bronchoalveolar lavage catheter.

25. A method as recited in claim 24, wherein said indication comprises a visually apprehendable signal.

26. A method as recited in claim 24, wherein said indication comprises an audible signal.

27. A method as recited in claim 1, wherein said step of advancing comprises the steps of:
(a) intubating the patient with an endotracheal tube; and
(b) inserting the distal end of the bronchoalveolar lavage catheter through said endotracheal tube into the air passageways of the patient.

28. A method as recited in claim 27, wherein said step of inserting is undertaken through an access port at the distal end of said endotracheal tube while maintaining positive expiratory end pressure.

29. A method as recited in claim 28, wherein said access port comprises a locking mechanism for selectively fixing the longitudinal position of the bronchoalveolar lavage catheter relative to the body of the patient.

30. A method as recited in claim 29, wherein said step of manipulating comprises the step of activating said locking mechanism when a condition of correct wedging of the distal tip of the bronchoalveolar lavage catheter has been confirmed in said step of monitoring.

31. A method as recited in claim 1, wherein one of said significant wedging-related conditions is a condition of correct wedging, and wherein said pressure waveform produced in said step of generating comprises a damped version of said pressure waveform.

32. A method as recited in claim 1, wherein one of said significant wedging-related conditions is a condition of ineffectual wedging, and wherein said pressure waveform produced in said step of generating comprises a substantially similar version of said pressure waveform.

33. A method as recited in claim 1, wherein one of said signification wedging-related conditions is a condition of precluded wedging, and wherein said pressure waveform produced in said step of generating comprises a substantially similar version of said pressure waveform.

34. A method as recited in claim 1, wherein one of said significant wedging-related conditions is a condition of overwedging, and wherein said pressure waveform produced in said step of generating comprises an over-damped version of said pressure waveform.

35. A method for conducting bronchoalveolar lavage with a bronchoalveolar lavage catheter of a portion of a lung of a patient, said method comprising the steps of:
(a) coupling a pressure transducer to the proximal end of the lumen of the bronchoalveolar lavage catheter, said bronchoalveolar lavage catheter comprising:

(e) a sampling catheter so sized and configured as to extend from a bronchiole in the lung of the patient through the upper respiratory system;
(ii) an elongated insertion sheath so sized and configured as to extend from below the bifurcation of the trachea of the patient through the upper respiratory system said insertion sheath possessing sufficient rigidity to be capable, when disposed in the upper respiratory system of a patient, of exhibiting at the distal end thereof one-to-one rotation about the longitudinal axis thereof relative to the proximal end thereof, said distal end of said insertion sheath being displaced at a predetermined bend angle to the longitudinal axis thereof; and
(iii) a tip disposed in the opening at the end of said sampling catheter capable of sealing the distal end of said insertion sheath when said sampling catheter is disposed in said insertion sheath with the distal end of said sampling catheter at the distal end of said insertion sheath;
(b) disposing said sampling catheter within said insertion sheath with said tip thereof sealing the distal end of said insertion sheath;
(c) advancing said insertion sheath with said sampling catheter disposed therein through the upper respiratory system of the patient to a point above and proximate to the first bifurcation of the trachea;
(d) rotating said proximal end of said insertion sheath, whereby said distal end thereof becomes oriented at said predetermined bend angle towards a preselected branch of the trachea;
(e) advancing said insertion sheath with said sampling catheter disposed therein into said preselected branch of the trachea;
(f) advancing said sampling catheter out of said insertion sheath into said preselected branch of the trachea;
(g) generating from the pressure transducer pressure waveforms reflective of air pressure variations in the air passageways of the patient distal of the tip of said sampling catheter;
(h) monitoring said pressure waveforms to detect therefrom the existence at the tip of said sampling catheter of significant wedging-related conditions of interest to medical personnel attempting to effect wedging of the distal tip of said sampling catheter; and
(i) manipulating the proximal end of said sampling catheter on the basis of said predetermined wedging-related conditions detected in said step of monitoring.

36. A method for as recited in claim 35, said step of monitoring comprising the steps of:
(a) developing a baseline pressure waveform for the patient reflecting air pressure variations in the air passageways of the patient distal of the tip of said sampling catheter due to ongoing, unobstructed ventilation of the patient; and
(b) comparing said baseline pressure waveform with pressure waveforms developed as the tip of said sampling catheter is advanced in the air passageways of the patient to detect characteristics in said pressure waveforms associated with each of said significant wedging-related conditions.

37. A method as recited in claim 35, wherein said significant wedging-related conditions comprise:
(a) a condition of correct wedging;

(b) a condition of ineffectual wedging;
(c) a condition of precluded wedging; and
(d) a condition of overwedging.

38. A method as recited in claim 35, wherein said step of advancing comprises the steps of:
(a) intubating the patient with an endotracheal tube; and
(b) inserting the distal end of the bronchoalveolar lavage catheter through said endotracheal tube into the air passageways of the patient.

39. A method as recited in claim 38, wherein said step of inserting is undertaken through an access port at the distal end of said endotracheal tube while maintaining positive expiratory end pressure.

40. A method as recited in claim 39, wherein said access port comprises a locking mechanism for selectively fixing the longitudinal position of the bronchoalveolar lavage catheter relative to the body of the patient.

41. A method for effecting wedging of a bronchoalveolar lavage catheter in a bronchiole in a lung of a patient, said method comprising the steps of:
(a) coupling a pressure transducer to the proximal end of the lumen of a bronchoalveolar lavage catheter;
(b) advancing the bronchoalveolar lavage catheter in the air passageways of the patient;
(c) generating from the pressure transducer pressure waveforms reflective of air pressure variations in the air passageways of the patient distal of the tip of the bronchoalveolar lavage catheter;
(d) monitoring said pressure waveforms to detect therefrom the existence at the tip of the bronchoalveolar lavage catheter of significant wedging-related conditions of interest to medical personnel attempting to effect wedging of the distal tip of the bronchoalveolar lavage catheter;
(e) informing medical personnel of the existence at the tip of the bronchoalveolar lavage catheter of said significant wedging-related conditions; and
(f) manipulating the proximal end of the bronchoalveolar lavage catheter on the basis of said predetermined wedging-related conditions detected in said step of monitoring.

42. A method as recited in claim 41, wherein said step of informing comprises the step of activating an indicator light.

43. A method as recited in claim 41, wherein said step of informing comprises the step of producing an audible tone.

44. A method as recited in claim 41, wherein said step of informing comprises the step of producing a pressure waveform on a cathode ray tube screen.

45. A method as recited in claim 41, wherein said step of informing comprises the step of producing a pressure waveform on a printout.

46. A system for conducting a bronchoalveolar lavage in a lung of a patient, said system comprising:
(a) a bronchoalveolar lavage catheter having centrally formed thereto a longitudinally extending first lumen and a distal tip; and
(b) verification means coupled to the proximal end of said first lumen of said broncholaveolar lavage catheter for monitoring air pressure variations in the air passageways of the patient distal of the distal tip of said bronchoalveolar lavage catheter.

47. A system as recited in claim 46, wherein said verification means comprises:
(a) an air pressure monitor; and
(b) means for coupling said air pressure monitor to the proximal end of said first lumen.

48. A system as recited in claim 47, wherein said air pressure monitor comprises:
(a) a pressure transducer; and
(b) display means electrically coupled to said pressure transducer for producing real time pressure waveforms corresponding to variations in air pressure in the air passageways of the patient distal of the distal tip of said bronchoalveolar lavage catheter.

49. A system as recited in claim 48, wherein said means for coupling comprises:
(a) an adaptor manifold secured on the proximal end of said bronchoalveolar lavage catheter; and
(b) a gas pressure tube coupled between said adaptor manifold and said pressure transducer.

50. A system as recited in claim 49, wherein said adapter manifold comprises a pressure stopcock, and a means, secured to said stopcock, for infusing and aspirating fluid through said bronchoalveolar lavage catheter, and said pressure stopcock being couplable to the proximal end of said bronchoalveolar lavage catheter and capable selectively of placing said first lumen therein alternately in communication with said gas pressure tube or with said means for infusing and aspirating fluid through said bronchoalveolar lavage catheter.

51. A system as recited in claim 49, wherein said adaptor manifold comprises a locking mechanism for selectively fixing the longitudinal position of the bronchoalveolar lavage catheter relative to the body of the patient.

52. A system as recited in claim 46, wherein said bronchoalveolar lavage catheter further comprises a second lumen and a flexible cuff attached to and encircling the sides of said bronchoalveolar lavage catheter proximal of the distal end thereof, said cuff being selectively inflatable to engage the walls of a bronchiole of the patient through said second lumen.

* * * * *

UNITED STATES PATENT AND TRADEMARK OFFICE
CERTIFICATE OF CORRECTION

PATENT NO. : 5,135,490
DATED : August 4, 1992
INVENTOR(S) : Richard D. Strickland It is certified that error appears in the above-indentified patent and that said Letters Patent is hereby corrected as shown below:

Column 1, line 18, delete "&"
Column 2, line 22, delete "$"
Column 3, line 8, after "produces" delete "of" and insert --in--
Column 3, line 8, after "circumference of the" insert --bronchoalveolar lavage catheter at or close to the tip. The--
Column 6, line 30, "Over inflation" should be --Overinflation--
Column 8, line 5, after "relation" insert --to a--
Column 8, line 56, "disclose" should be --disclosed--
Column 9, line 9, after "as" insert --to--

Column 10, line 61, "be" should be --by--
Column 12, line 27, after "aspiration" insert --of sampling fluid as required for bronchoalveolar lavage can--
Column 14, line 45, delete "of"
Column 19, line 54, after "132" insert --.--
Column 19, line 65, "born" should be --borne--
Column 26, line 1, "(e)" should be --(i)--

Signed and Sealed this

Eighteenth Day of January, 1994

Attest:

BRUCE LEHMAN

Attesting Officer

Commissioner of Patents and Trademarks